(12) United States Patent
He et al.

(10) Patent No.: US 11,835,479 B2
(45) Date of Patent: *Dec. 5, 2023

(54) SYSTEMS, DEVICES, AND METHODS FOR RF DETECTION OF ANALYTE SENSOR MEASUREMENTS

(71) Applicant: ABBOTT DIABETES CARE INC., Alameda, CA (US)

(72) Inventors: Lei He, Moraga, CA (US); Michael R. Love, Pleasanton, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/349,072

(22) Filed: Jun. 16, 2021

(65) Prior Publication Data

US 2022/0099611 A1 Mar. 31, 2022

Related U.S. Application Data

(63) Continuation of application No. PCT/US2019/064724, filed on Dec. 5, 2019.

(60) Provisional application No. 62/781,972, filed on Dec. 19, 2018.

(51) Int. Cl.
*G01N 29/02* (2006.01)
*G01N 27/02* (2006.01)
*G01R 23/02* (2006.01)
*H01Q 1/22* (2006.01)
*H01Q 7/00* (2006.01)

(52) U.S. Cl.
CPC ........... *G01N 27/028* (2013.01); *G01R 23/02* (2013.01); *H01Q 1/2208* (2013.01); *H01Q 7/00* (2013.01)

(58) Field of Classification Search
CPC .............................. G01R 23/02; G01N 27/028
See application file for complete search history.

(56) References Cited

U.S. PATENT DOCUMENTS

| 5,262,035 A | 11/1993 | Gregg et al. |
| 6,480,007 B1 | 11/2002 | Beck et al. |
| 6,565,509 B1 | 5/2003 | Say et al. |
| 6,654,470 B1 * | 11/2003 | Dilger .................. G01N 29/022 381/94.1 |
| 8,808,515 B2 | 8/2014 | Ouyang et al. |
| 2007/0173710 A1 | 7/2007 | Petisce et al. |
| 2008/0009692 A1 | 1/2008 | Stafford |
| 2009/0259112 A1 | 10/2009 | Hyde et al. |

(Continued)

FOREIGN PATENT DOCUMENTS

WO WO 2019/005301 A1 1/2019

OTHER PUBLICATIONS

WO, PCT/US2019/064724 ISR and Written Opinion, dated Apr. 7, 2020.
EP, 19899938.5 Extended Search Report, dated Aug. 19, 2022.

*Primary Examiner* — Alesa Allgood
(74) *Attorney, Agent, or Firm* — ONE LLP

(57) ABSTRACT

Embodiments that translate a sensor measurement to a frequency characteristic are disclosed. The frequency characteristic can be wirelessly detected by a reader device. The detected frequency characteristic can be used to determine the corresponding sensor measurement. Devices utilizing this approach can be characterized or calibrated to increase accuracy. Systems and methods utilizing the approaches are also described.

19 Claims, 16 Drawing Sheets

(56) References Cited

U.S. PATENT DOCUMENTS

| | | |
|---|---|---|
| 2010/0171368 A1 | 7/2010 | Schatz et al. |
| 2010/0213082 A1 | 8/2010 | Feldman et al. |
| 2011/0068807 A1* | 3/2011 | Kesil .................... G01N 27/023 |
| | | 324/633 |
| 2011/0193704 A1 | 8/2011 | Harper et al. |
| 2011/0213225 A1 | 9/2011 | Bernstein et al. |
| 2011/0319729 A1 | 12/2011 | Donnay et al. |
| 2012/0116683 A1 | 5/2012 | Potyrailo et al. |
| 2013/0141117 A1* | 6/2013 | Nikolenko ............. G01R 27/16 |
| | | 324/655 |
| 2014/0062666 A1* | 3/2014 | Patterson ........... G06K 7/10366 |
| | | 340/10.1 |
| 2015/0018639 A1 | 1/2015 | Stafford |
| 2015/0025345 A1 | 1/2015 | Funderburk et al. |
| 2015/0173661 A1 | 6/2015 | Myles |
| 2015/0182153 A1 | 7/2015 | Feldman et al. |

* cited by examiner

SYSTEMS, DEVICES, AND METHODS FOR RF DETECTION OF ANALYTE SENSOR MEASUREMENTS

CROSS-REFERENCE TO RELATED APPLICATIONS

The present application is a continuation of International Patent Application Serial No. PCT/US19/64724, filed Dec. 5, 2019, which claims priority to and the benefit of U.S. Provisional Patent Application Ser. No. 62/781,972, filed Dec. 19, 2018, both of which are incorporated by reference herein in their entireties for all purposes.

FIELD

The subject matter described herein relates generally to systems, devices, and methods for detection of an analyte sensor measurement using RF frequency resonance.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

For these and other reasons, needs exist for improved analyte monitoring systems, devices, and methods.

SUMMARY

Example embodiments of systems, devices, and methods are described herein for determining analyte levels by detecting a frequency characteristic of an on body device. In many embodiments this frequency characteristic is a resonance or resonant frequency. The on body device can include an analyte sensor adapted to sense the analyte level in the body of a wearer and translate the analyte level to a resonance frequency. A separate device can wirelessly transmit an electromagnetic field at a range of frequencies and determine the resonance frequency based on the response received from the on body device. These embodiments can simplify the design of on body devices and/or reduce the cost associated therewith, by allowing removal of components such as an on-board power supply, a processor, and the like. Numerous example embodiments of hardware and software for use in determining the resonance frequency and corresponding analyte level are provided. Also provided are numerous example embodiments of calibrating or characterizing the devices to increase the accuracy of the frequency and/or analyte determinations.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1A:
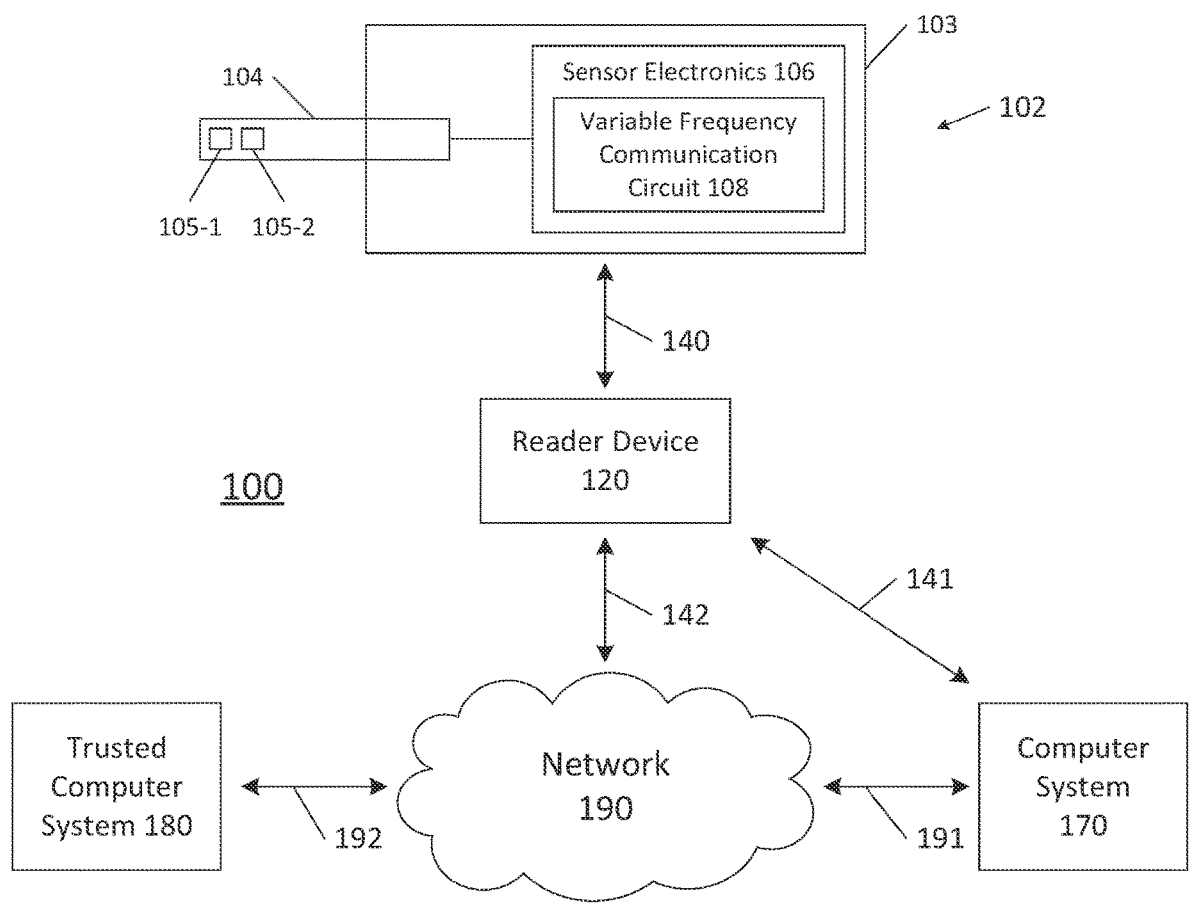
FIG. 1A is a block diagram depicting an example embodiment of an in vivo analyte monitoring system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Generally, embodiments of the present disclosure are used with systems, devices, and methods for detecting at least one analyte, such as glucose, in a bodily fluid (e.g., subcutaneously within the interstitial fluid ("ISF") or blood, within the dermal fluid of the dermal layer, or otherwise). Accordingly, many embodiments include in vivo analyte sensors structurally configured so that at least a portion of the sensor is, or can be, positioned in the body of a user to obtain information about at least one analyte of the body. However, the embodiments disclosed herein can be used with in vivo analyte monitoring systems that incorporate in vitro capability, as well as purely in vitro or ex vivo analyte monitoring systems, including those systems that are entirely non-invasive.

Example Embodiments of Analyte Monitoring Systems

In vivo analyte monitoring systems can include a sensor that, while positioned in vivo, makes contact with the bodily fluid of the user and senses one or more analyte levels contained therein. The sensor can be part of an on body device that resides on or in the body of the user. In addition to the sensor, the on body device can include circuitry that interfaces with the sensor, e.g., to convert a sensor measurement to a detectable radio frequency (RF) characteristic.

The on body device, and variations thereof, can also be referred to as a "sensor device," an "on-body electronics device," or a "sensor communication device", to name a few. As used herein, these terms are not limited to devices with in vivo analyte sensors, and encompass devices that have ex vivo sensors of other types, whether biometric (e.g., photonic analyte sensors, heart rate sensors, temperature sensors, etc.) or non-biometric. The term "on body" encompasses devices that reside directly on the body (e.g., attached to the skin), are wholly within the body (e.g., a fully implanted device), or are in close proximity to the body, such as a wearable device (e.g., glasses, watch, wristband or bracelet, neckband or necklace, etc.).

In vivo monitoring systems can also include one or more reader devices that read information about a sensed level from the on body device. These reader devices can process and/or display the sensed analyte information, in any number of forms, to the user. These devices, and variations thereof, can be referred to as "handheld reader devices," "readers," "handheld electronics" (or handhelds), "portable data processing" devices or units, "information receivers," "receiver" devices or units (or simply receivers), "relay" devices or units, or "remote" devices or units, to name a few.

In vivo analyte monitoring systems can be differentiated from "in vitro" systems that contact a biological sample outside of the body, and "ex vivo" systems that gain information about the body or a substance within the body but that do so while remaining wholly outside the body without extracting a biological sample from inside the body. In vitro systems can include a meter device that has a port for receiving an analyte test strip carrying a bodily fluid of the user, which can be analyzed to determine the user's analyte level. As mentioned, the embodiments described herein can be used with in vivo systems, ex vivo systems, in vitro systems, and combinations thereof.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times FIG. 1A is a block diagram depicting an example embodiment of an in vivo analyte monitoring system 100 having an on body device 102 ("OBD") and a reader device 120 that can communicate with each other wirelessly over path 140. OBD 102 can include a housing 103 encompassing sensor electronics 106 communicatively coupled with analyte sensor 104, which is configured for in vivo analyte monitoring.

Analyte sensor 104 can be located wholly outside of housing 103 or partially outside of housing 103 (as shown in FIG. 1A), and can include one or more electrodes 105 (e.g., one, two, three, or more) for contact with the user's bodily tissue or fluid. In the embodiment of FIG. 1A, sensor 104 includes two electrodes: a working electrode 105-1 and a counter (or reference) electrode 105-2. The chemical and mechanical construction of electrochemical analyte sensors, and operation thereof, is known to those of ordinary skill in the art. Some non-limiting examples of analyte sensors 104 that can be used with the embodiments of system 100 are described in the following references, all of which are incorporated by reference in their entirety and for all purposes: U.S. Publ. No. 2010/0213082 ("Self-Powered Analyte Sensor"), U.S. Publ. No. 2015/0182153 ("Self-Powered Analyte Sensor and Devices Using the Same"), U.S. Publ. No. 2007/0173710 ("Membranes for an Analyte Sensor"), U.S. Pat. No. 5,262,035 ("Enzyme Electrodes"), U.S. Pat. No. 6,565,509 ("Analyte Monitoring Device and Methods of Use"), and U.S. Pat. No. 8,808,515 ("Heterocyclic nitrogen containing polymers coated analyte monitoring device and methods of use").

Electrochemical sensors 104 often require the application of a voltage to permit the electrochemical analyte sensing reaction to occur. This voltage is sometimes referred to as a bias or poise voltage. This bias voltage can be supplied to sensor 104 by an artificial power supply (e.g., a battery) external to the sensor itself. The power supply is included within OBD 102 along with other circuitry for managing power usage. However, these extra components add complexity and cost to the design and manufacture of OBD 102, and also can impact the shelf life and wear duration of OBD 102.

Embodiments of OBD 102 can operate without and optionally omit an artificial power supply (e.g., a battery) external to the sensor and any additional circuitry responsible for management (e.g., connection and disconnection) of the power supply. For example, certain types of electrochemical sensors 104 are capable of measuring analyte levels without a power supply external to the sensor (e.g., a discrete battery such as a button cell or coin cell battery, or others) that provides the bias voltage. Such sensors 104 are sometimes referred to as continually self-biased sensors or self-powered sensors, and examples of these sensors are described in the incorporated U.S. Publ. No. 2010/0213082 ("Self-Powered Analyte Sensor") and/or U.S. Publ. No. 2015/0182153 ("Self-Powered Analyte Sensor and Devices Using the Same"). Continually self-biased sensors can, e.g., measure analyte levels with power spontaneously generated by the sensor itself upon insertion into the user's body using electrochemical reactants on the sensor's electrodes. Embodiments of OBD 102 that incorporate, for example, such a continually self-biased sensor can include no power supply external to the sensor, and this can in turn reduce the complexity and cost of OBD 102, as well as improve the shelf life and wear duration of OBD 102.

In some embodiments OBD 102 can include a power supply external to the sensor as well as transistor-based logic requiring an active bias for operation (e.g., an analog to digital converter, digital to analog converter, microcontroller, processor, digital signal processor, ASIC, and the like) such as that typically fabricated on a semiconductor chip and mounted on a printed circuit board. In these and other embodiments OBD 102 can include active communication circuitry (e.g., circuitry for generating transmissions spontaneously according to a wireless protocol such as Bluetooth, Bluetooth Low Energy, Wi-Fi, proprietary protocols (e.g., in a UHF band), and the like).

In other embodiments, it is desirable to minimize the cost and complexity of OBD 102. In these other embodiments, a power supply can be omitted from OBD 102, as well as some or all active circuitry. OBD 102 can include only passive transistor circuitry that does not require the presence of a continual bias for operation. Examples of transistor-based active circuitry that can be omitted include any and all of, e.g., an analog to digital converter, digital to analog converter, microcontroller, processor, digital signal processor, ASIC, volatile memory, circuitry for generating transmissions spontaneously (e.g., without prompting or power harvesting) according to a wireless protocol such as Bluetooth, Bluetooth Low Energy, Wi-Fi, proprietary protocols (e.g., in a UHF band), and the like. The omission of the power source and active circuitry can be the result of, in some examples, reliance upon power generated by a continually self-biased sensor to change a resonance frequency of variable frequency circuit 108, the frequency of which can be detected passively by an actively transmitting interrogation device (such as reader device 120). Other approaches not relying on a continually self-biased sensor can also be used. Also, in some embodiments OBD 102 can omit a power supply and instead utilize a charge storing device (e.g., a capacitor bank) that can store charge harvested from other sources, like from a wireless RF signal or inductive coupling (e.g., NFC) or from the sensor operation itself (e.g., as with a self-biased sensor).

An insertion device (not shown) can be used to position all or a portion of analyte sensor 104 through an external surface of the user's skin and into contact with the user's bodily fluid. In doing so, the insertion device can also position OBD 102 with adhesive patch 107 onto the skin. In other embodiments, the insertion device can position sensor 104 first, and then accompanying sensor electronics (e.g., a transmitter) can be coupled with sensor 104 afterwards, either manually or with the aid of a mechanical device. Examples of insertion devices are described in U.S. Publ. Nos. 2008/0009692, 2011/0319729, 2015/0018639, 2015/ 0025345, and 2015/0173661, all which are incorporated by reference herein in their entireties and for all purposes.

Figure 1B:
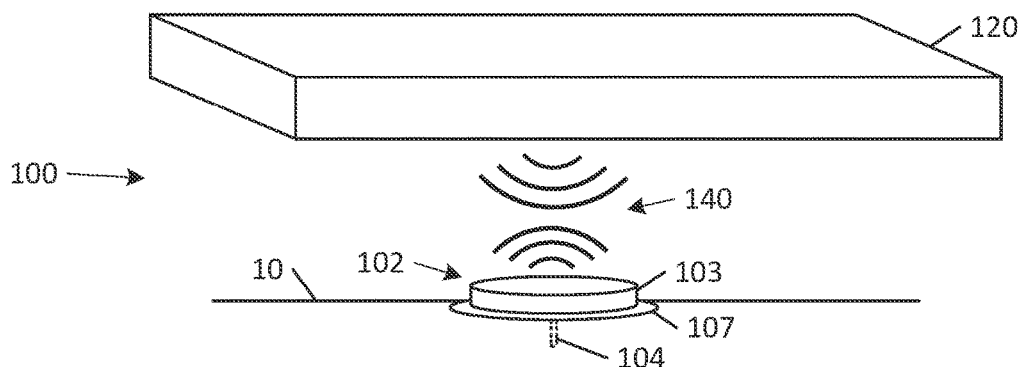
FIG. 1B is an illustrative view depicting an example embodiment of an analyte monitoring system with an on body device mounted on the body of a human user.

FIG. 1B is an illustrative view depicting an example embodiment of system 100 with OBD 102 mounted on the skin or body 10 of a human user with a portion of analyte sensor 104 inserted into the body (shown dashed). Housing 103 of OBD 102 can be coupled with a flexible patch 107, which can have adhesive on an underside surface to adhesively couple OBD 102 to the user's body 10. A topside surface of patch 107 can also include adhesive for coupling with housing 103. Other forms of body attachment to the body may be used, in addition to or instead of adhesive. Analyte sensor 104 can extend from within housing 103, through patch 107 and project away from housing 103. A handheld or portable reader device 120 is shown in close proximity with OBD 102 for wireless communication over path 140.

After insertion, analyte sensor 104 can generate and output a signal or stimulus that is based upon (e.g., in relation to, in proportion to, directly or indirectly corresponding to, or others) the level of the analyte in body 10 that is measured with the one or more electrodes 105. This sensor output can be, e.g., an electrical voltage or current. Sensor electronics 106 can include a variable frequency circuit 108. The sensor output is provided to circuit 108, and a frequency characteristic of circuit 108 can be varied, modified, or changed automatically based upon (e.g., in relation to, in proportion to, directly or indirectly corresponding to, or others) a characteristic of the sensor output (e.g., a current magnitude and/or polarity, a voltage magnitude and/or polarity, or others).

In many embodiments, reader device 120 can generate an electromagnetic field at one or more frequencies and detect the frequency characteristic (e.g., a resonance frequency) of variable frequency circuit 108 of OBD 102 by inductively coupling with circuit 108. To establish the inductive coupling, reader device 120 is, in many embodiments, placed in close proximity with OBD 102 (e.g., within a few feet or a few inches as depicted in FIG. 1B). While the range is dependent upon output power, receiver sensitivity and the antennas, in some embodiments, reader device 120 is positioned within 30 centimeters (cm) of OBD 102 to establish the inductive coupling. In other embodiments, the range of reader device 120 is shorter, for example, 3 cm or less. Reader device 120 can use the detected frequency characteristic to determine the measured analyte level and output (e.g., display) the analyte level to the user.

As mentioned above, OBD 102 can also be placed wholly within the body (e.g., a fully implanted device). In such embodiments, reader 120 can read the analyte level through the skin and/or other body tissue and fluid. Reader 120 can be manually held in close proximity to OBD 102 and/or can be held in place or worn over OBD 102 by a band or strap (e.g., armband, bracelet, neckband, waistband or belt, etc.) or other attachable device, such as an adhesive-based device.

Referring back to FIG. 1A, reader device 120 can communicate the measured analyte level to other devices within system 100. For example, reader device 120 can be capable of wired, wireless, or combined communication with a computer system 170 (local or remote) over communication path (or link) 141. In embodiments where path 141 is wireless, a Wi-Fi protocol, Bluetooth or Bluetooth Low Energy protocol, a near field communication (NFC) protocol, RFID protocol, proprietary protocol, or others can be used. Reader device can also communicate with or through a network 190 (e.g., such as a mobile telephony network, the internet or the cloud) over communication path (or link) 142.

Communication through network 190 can include communications sent to and from computer system 170 via communication link (or path) 191, communications sent to and from trusted computer system 180 over communication path (or link) 192, and/or communications to other devices. Communication paths 141, 142, 191, and 192 can be wireless, wired, or both, can be uni-directional or bi-directional, and can be direct or indirect through intermediaries. In some embodiments, communication paths 141 and 142 can be the same path. Example embodiments of reader device 120 are described in further detail herein. Further example embodiments are described in U.S. Publ. No. 2011/0213225 (the '225 Publication), which is incorporated by reference herein in its entirety for all purposes. While only one reader 120 is shown, there can be one or more readers 120 that can interrogate device 102 and each reader 120 can communicate and share data with one another.

Computer system 170 may be another reader device 120, a personal computer, a server terminal, a laptop computer, a tablet, or other suitable data processing device. Computer system 170 can be (or include) software for analyte data management and analysis and communication with the components in analyte monitoring system 100. Computer system 170 can be used by the user or a medical professional to display and/or analyze the biometric data measured by OBD 102. In some embodiments, OBD 102 can communicate the biometric data directly to computer system 170 without an intermediary such as reader device 120, or indirectly using an internet connection (also optionally without first sending to reader device 120). Operation and use of computer system 170 are further described in the '225 Publication incorporated herein. Analyte monitoring system 100 can also be configured to operate with a data processing module (not shown), also as described in the incorporated '225 Publication.

Trusted computer system 180 can be within the possession of the manufacturer or distributor of OBD 102, either physically or virtually through a secured connection, and can be used to perform authentication of OBD 102, to provide one or more calibration values for OBD 102, used for secure storage of the user's biometric data, used for provision of software updates or revisions, used as a server that serves a data analytics program (e.g., accessible via a web browser) for performing analysis on the user's measured data, or other functions.

Example Embodiments of Converting an Analyte Measurement to a Resonance Frequency Examples embodiments of OBD 102 are capable of varying a frequency characteristic based upon a sensor measurement that corresponds to the user's analyte (e.g., glucose) level. The sensor measurement can be in the form of an electrical signal, such as a current or voltage. The electrical signal can vary with the analyte level in linear or non-linear fashion. For example, the sensor current can increase proportionally with the concentration of analyte in the bodily fluid being measured. Variable frequency circuit 108 can have a frequency characteristic that varies linearly or non-linearly with the electrical signal. This relationship can be direct (e.g., such that the value of the frequency characteristic increases as the electrical signal output from the sensor increases) or indirect (e.g., such that the value of the frequency characteristic increases as the electrical signal output from the sensor decreases).

Figure 2A:
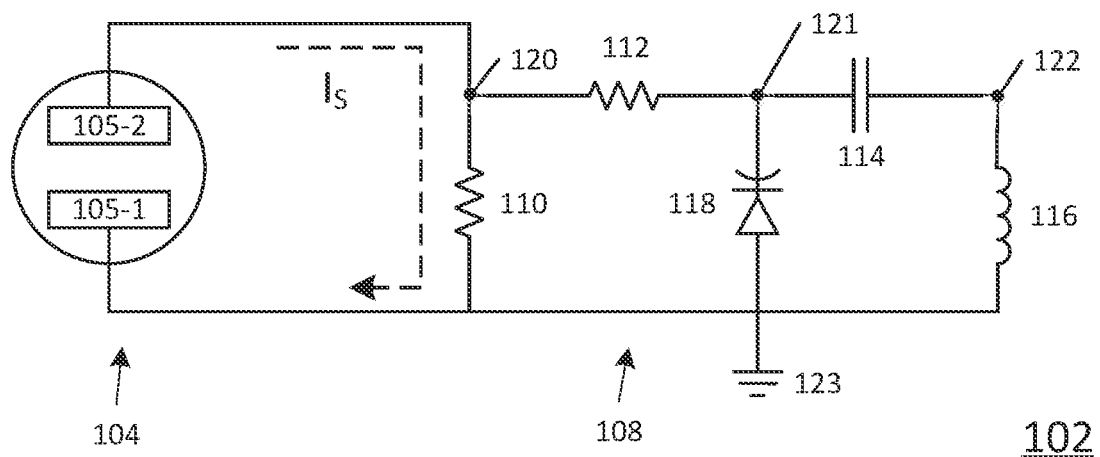
FIG. 2A is a schematic diagram depicting an example embodiment of components of an on body device.

FIG. 2A is a schematic diagram of an example embodiment of components of OBD 102. Here, OBD 102 includes analyte sensor 104 electrically coupled with variable frequency circuit 108. In this embodiment, analyte sensor 104 is a continually self-biased sensor that includes a working electrode 105-1 and a counter electrode 105-2 (the locations of which can be reversed). Power for OBD 102 is generated by the continually self-biased sensor 104 and no power supply external to sensor 104 is required (and can either be omitted or included depending upon the needs of the application).

Variable frequency circuit 108 can be configured in numerous ways. Here, circuit 108 is configured as an RLC circuit with a variable impedance. Circuit 108 includes a first resistor 110 coupled between electrodes 105-1 and 105-2. A second resistor 112 is coupled between node 120 (between resistor 110 and electrode 105-2) and node 121. A capacitor 114 is coupled between node 121 and node 122. An inductor 116 is coupled between node 122 and node 123 (indicated here as ground). The resistive value of resistors 110 and 112 can be derived from the presence of a discrete resistive component and/or the inherent resistance of conductive wires, traces, or components (or portions thereof) forming circuit 108. Similarly, the capacitance value of capacitor 114 can be derived from the presence of a discrete component exhibiting capacitance (e.g., a capacitor) and/or the inherent capacitance of conductive wires, traces, or components (or portions thereof) forming circuit 108. Inductor 116 can include an antenna configured to inductively couple with an interrogating transmission device (e.g., reader 120). The antenna can be configured as, for example, a loop antenna (with one or more circular loops, polygonal loops, or combinations thereof). Other antenna configurations can also be used. The inductive value of inductor 116 is derived from the inductance of the antenna, and can also be derived from the presence of a discrete inductive component and/or the inherent inductance of conductive wires, traces, or components (or portions thereof) forming circuit 108.

A variable impedance component 118 is coupled between node 121 and node 123. Variable impedance component 118 has an impedance that changes with the electrical stimulus applied to it. In many embodiments, variable impedance component 118 is a variable capacitor having a capacitance that changes in response to a voltage applied across it. The variable capacitor can be, for example, a varactor diode as shown here with its cathode coupled to node 121 and its anode connected to node 123. Varactor diodes can exhibit voltage dependent capacitance when operated in a reverse biased state. Other types of variable impedance components can also be used, such as other devices that exhibit variable capacitance and devices that exhibit variable inductance. Several examples include but are not limited to metal-oxide semiconductor field-effect transistors (MOSFETs) and bipolar transistors.

During operation, sensor 104 generates a current (Is) that flows through resistor 110. The magnitude of the current is based upon the level of the analyte being measured in the wearer's body. A voltage is exhibited across resistor 110 based upon the magnitude of the current (V=IR). A corresponding voltage is applied across varactor diode 118. The magnitude of the voltage applied across varactor diode 118 is proportional to that applied across resistor 110 but may differ depending on the resistance of resistor 112. The capacitance exhibited by varactor diode 118 is dependent upon the voltage applied across diode 118, which in turn is dependent upon the magnitude of the current generated by the sensor.

Circuit 108 exhibits a frequency characteristic, such as a resonance frequency, that is dependent upon the impedance of circuit 108, as determined by the fixed capacitance of capacitor 114, the fixed inductance of inductor 116, and the variable capacitance of varactor diode 118. As the capacitance of varactor diode 118 changes, so does the resonance frequency of circuit 108. The resonance frequency of circuit 108 is given by the equation (1) below:

$$f = \frac{1}{2\pi\sqrt{LC}}$$

where f is the resonance frequency in hertz, L is the inductance of component 116 in henrys, and C is the total capacitance in farads. In FIG. 2A, the total capacitance is determined by the fixed capacitor 114 and the varying capacitance of diode 118. A change in Is causes a change in the variable capacitance of diode 118, which in turn changes the resonance frequency of the circuit.

Figure 2B:
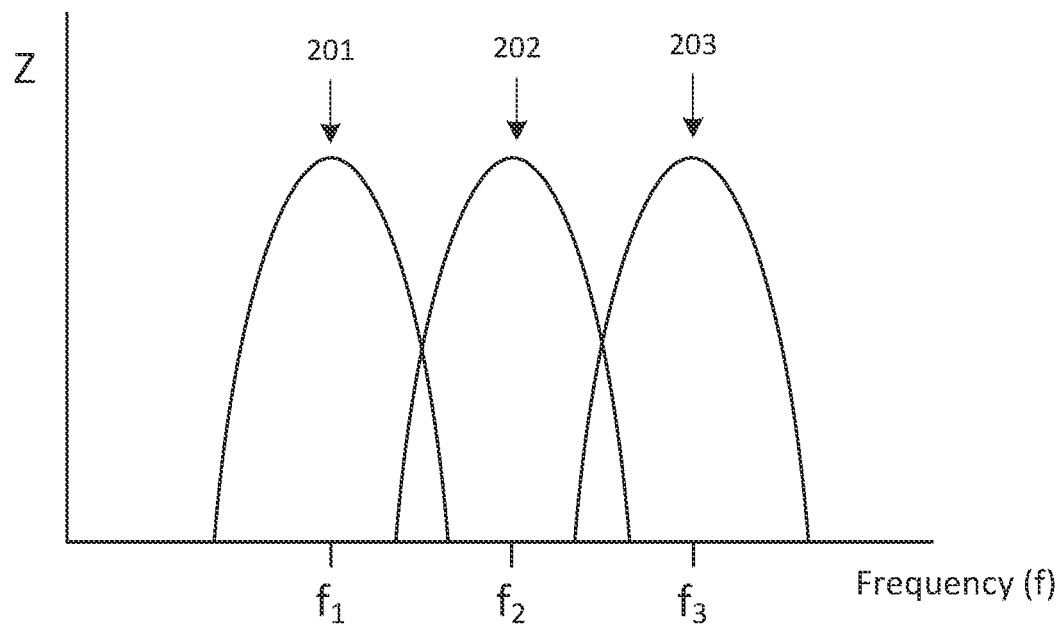
FIG. 2B is a plot depicting examples of LC resonance frequency responses exhibited by on body device circuitry.

FIG. 2B is a plot depicting examples of three different LC resonance frequency responses exhibited by circuit 108 with three different voltages applied across varactor diode 118. Here, circuit 108 can exhibit a first resonance frequency response 201 having a center frequency f1 when a first voltage is applied across varactor diode 118, a second resonance frequency response 202 having a center frequency f2 when a second voltage is applied across diode 118, and a third resonance frequency response 203 having a center frequency f3 when a third voltage is applied across diode 118. Each residence frequency response is dependent upon the current generated by sensor 104, which in turn is dependent upon the level of analyte in the user's body. Thus, OBD 102 can exhibit a frequency response that is dependent upon the user's sensed analyte level. As mentioned, circuit 108 can be configured such that the resonance frequency response either increases or decreases with an increase to the user's analyte level.

Figure 2C:
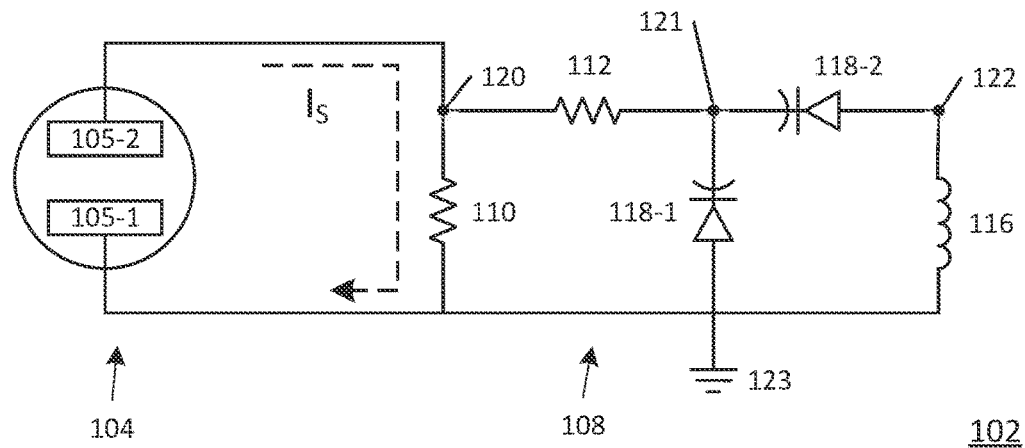
FIGS. 2C-2D are schematic diagrams depicting additional example embodiments of components of an on body device.

The number and arrangement of components of OBD 102 can vary, depending on the desired frequency response. For example, in the embodiments described herein an additional capacitor can be added in parallel with varactor diode 118 (e.g., between node 121 and 123). FIG. 2C is a schematic diagram of another example embodiment of OBD 102 where a second variable capacitor 118-2 (e.g., varactor diode) is used in place of capacitor 114 of FIG. 2A. In this embodiment the DC voltage at node 121 is also applied to varactor diode 118-2, which increases the potential capacitance change of the circuit.

Figure 2D:
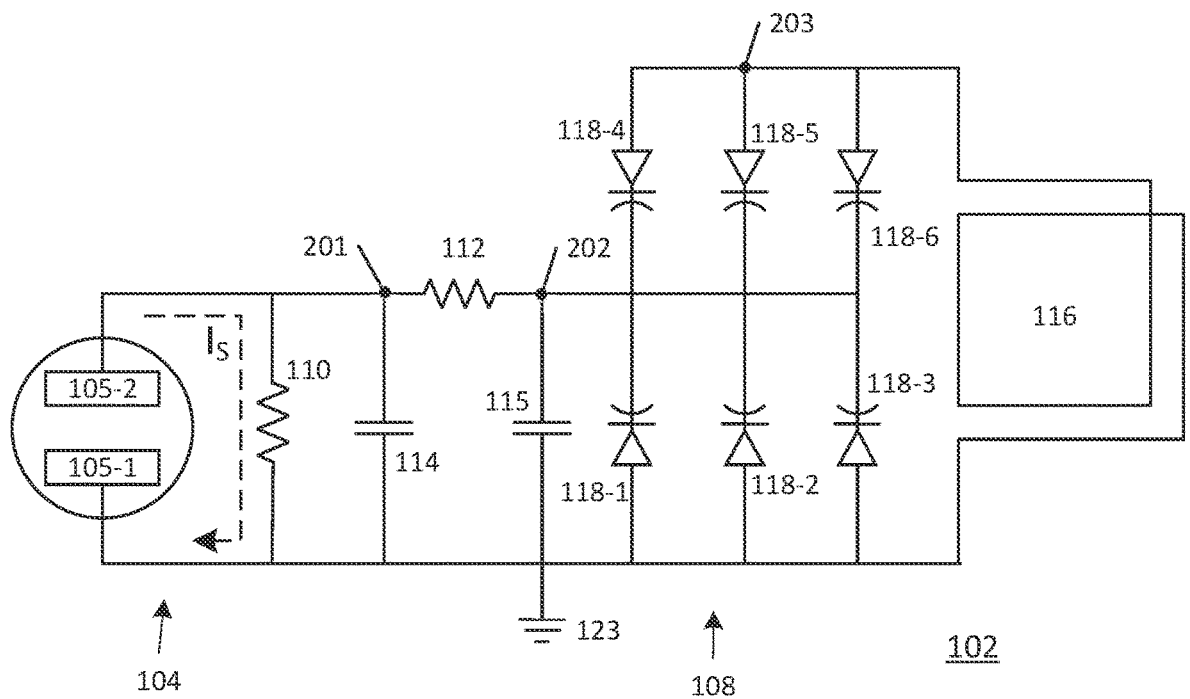

FIG. 2D is a schematic diagram of another example embodiment of OBD 102. Like the embodiment of FIG. 2A, in this embodiment analyte sensor 104 can be a continually self-biased sensor that generates power for OBD 102 without a power supply external to sensor 104. Here, capacitor 114 is in parallel with resistor 110 between nodes 201 and 123. Resistor 112 is coupled between nodes 201 and 202. A second capacitor 115 is coupled between nodes 202 and 123. As with capacitor 114, the capacitance value of capacitor 115 can be derived from the presence of a discrete component exhibiting capacitance (e.g., a capacitor) and/or the inherent capacitance of conductive wires, traces, or components forming circuit 108.

Instead of a single varactor diode 118, the embodiment of FIG. 2D includes multiple varactor diodes 118-1 through 118-6. Varactor diodes 118-1, 118-2, and 118-3 are in parallel with each other with their cathodes connected to node 202 and their anodes connected to node 123 and form a first bank. Varactor diodes 118-4, 118-5, and 118-6 are also in parallel with each other and have their cathodes connected to node 202 and their anodes connected to node 203 and form a second bank. Inductor 116 in the form of a loop antenna is coupled between nodes 203 and 123. The frequency range of this embodiment for a given voltage range is relatively higher than the embodiment of FIG. 2A. The resistance of the antenna 116 is preferably nearly zero or negligible, such that both banks of diodes 118 see the same or substantially the same voltage change, and can be conceptualized as one bank of parallel diodes 118. A true parallel arrangement can also be used (e.g., with all six cathodes coupled with node 202 and all six anodes coupled with node 123) provided a capacitor or other DC block is in series with inductor 116. The component tolerance of diodes 118-1 through 118-6 is averaged, and the capacitance of the diodes within each bank are summed together. Thus, the range of capacitance change in circuit 108 can be increased as compared to an embodiment having one diode 118 and one fixed capacitor 114.

Example Embodiments of Interrogation Circuits and Reader Devices

Figure 3A:
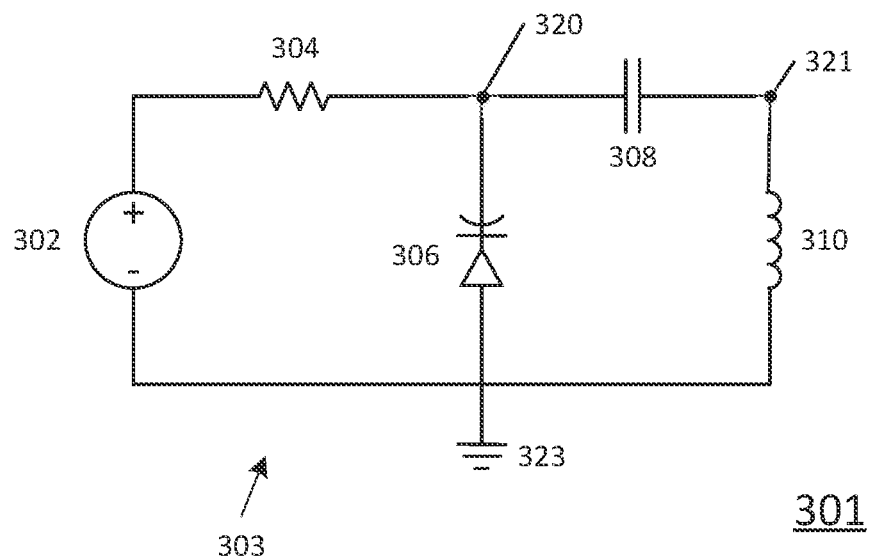
FIG. 3A is a schematic view depicting an example embodiment of a variable frequency circuit within a reader device.

Detection of the resonance frequency can be accomplished by use of an interrogation device, such as reader device 120. FIG. 3A is a schematic view depicting an example embodiment of a variable frequency circuit 301 that can be present within reader device 120. Circuit 301 can include a variable DC source 302 coupled with a variable impedance (e.g., RLC) circuit 303 that includes a resistor 304 coupled between the source and a node 320, a variable impedance component 306 coupled between node 320 and node 323 (e.g., ground), a capacitor 308 coupled between node 320 and 321 and an inductor 310 coupled between node 321 and node 323. In this embodiment, the variable impedance component 306 is a varactor diode with its cathode coupled to node 320 and its anode coupled to node 323. Any arrangement of one or more varactor diodes 306 can be used in serial, parallel, or combination thereof.

The resistive value of resistor 304 can be derived from the presence of a discrete resistive component and/or the inherent resistance of conductive wires, traces, or components (or portions thereof) forming circuit 301. Similarly, the capacitance value of capacitor 308 can be derived from the presence of a discrete component exhibiting capacitance (e.g., a capacitor) and/or the inherent capacitance of conductive wires, traces, or components (or portions thereof) forming circuit 301. Inductor 310 can include an antenna configured to inductively couple with circuit 108. The antenna can be configured as, for example, a loop antenna (with one or more circular loops, polygonal loops, or combinations thereof). Other antenna configurations can also be used. The inductive value of inductor 310 is derived from the inductance of the antenna, and can also be derived from the presence of a discrete inductive component and/or the inherent inductance of conductive wires, traces, or components (or portions thereof) forming circuit 301.

Application of a DC voltage from source 302 to circuit 303 will apply a voltage across varactor diode 306 and cause it to assume a capacitive value. That capacitive value will determine the impedance and a corresponding resonance frequency of circuit 303. When variable frequency circuit 301 is in proximity with variable frequency circuit 108, application of an RF frequency or set of RF frequencies to circuit 301 (such as with an RF generator) can cause circuits 108 and 301 to inductively couple where inductance of circuit 108 is reflected into circuit 301. The inductive coupling can allow the resonance frequency of circuit 108 to be detected as will be described in more detail below.

Figure 3B:
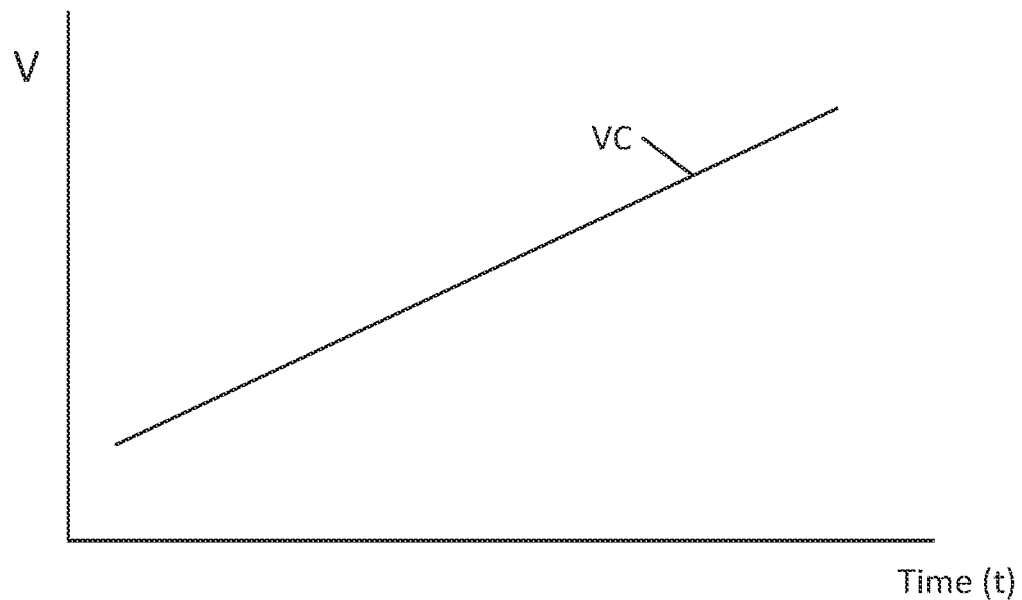
FIG. 3B is a plot of an example where a control voltage increases continuously over time (t).
Figure 3C:
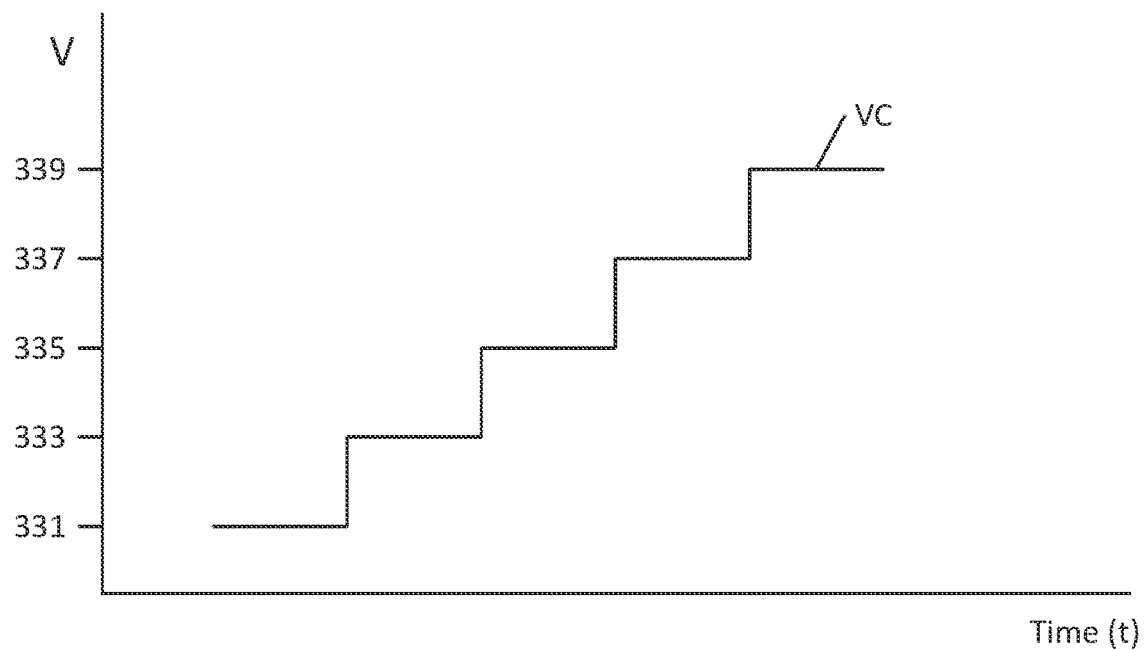
FIG. 3C is a plot of another example where a control voltage is increased over time (t) in a stepped fashion.
Figure 3D:
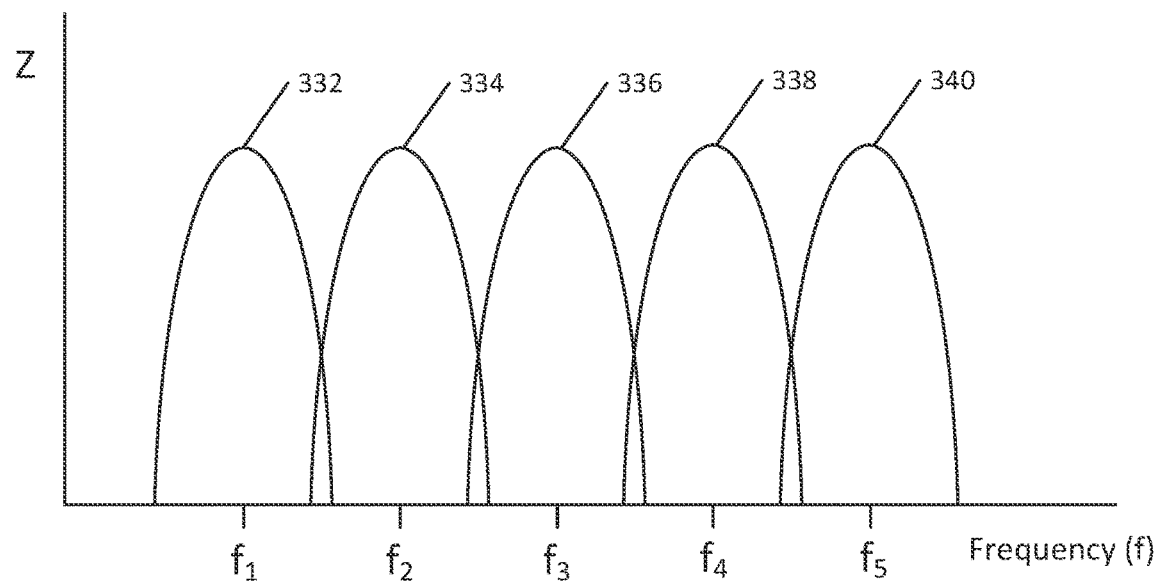
FIG. 3D is plot of an example frequency response of a variable frequency circuit to the stepped voltages depicted in FIG. 3C.

The control voltage (VC), e.g., the voltage output from DC source 302, can be adjusted to cause the impedance and resonance frequency of circuit 303 to change. FIG. 3B is a plot of an example where VC increases continuously over time (t) at a constant rate, which has the effect of changing the resonance frequency of circuit 303 at a similar rate. FIG. 3C is a plot of another example where VC is increased over time (t), but here the increase occurs in a stepped fashion. This causes the resonance frequency of circuit 303 to jump from one value and settle on another. FIG. 3D is plot of an example frequency response of circuit 303 to the stepped voltages depicted in FIG. 3C. In this embodiment, voltage 331 results in frequency response 332, voltage 333 results in frequency response 334, voltage 335 results in frequency response 336, voltage 337 results in frequency response 338, and voltage 339 results in frequency response 340.

Figure 4:
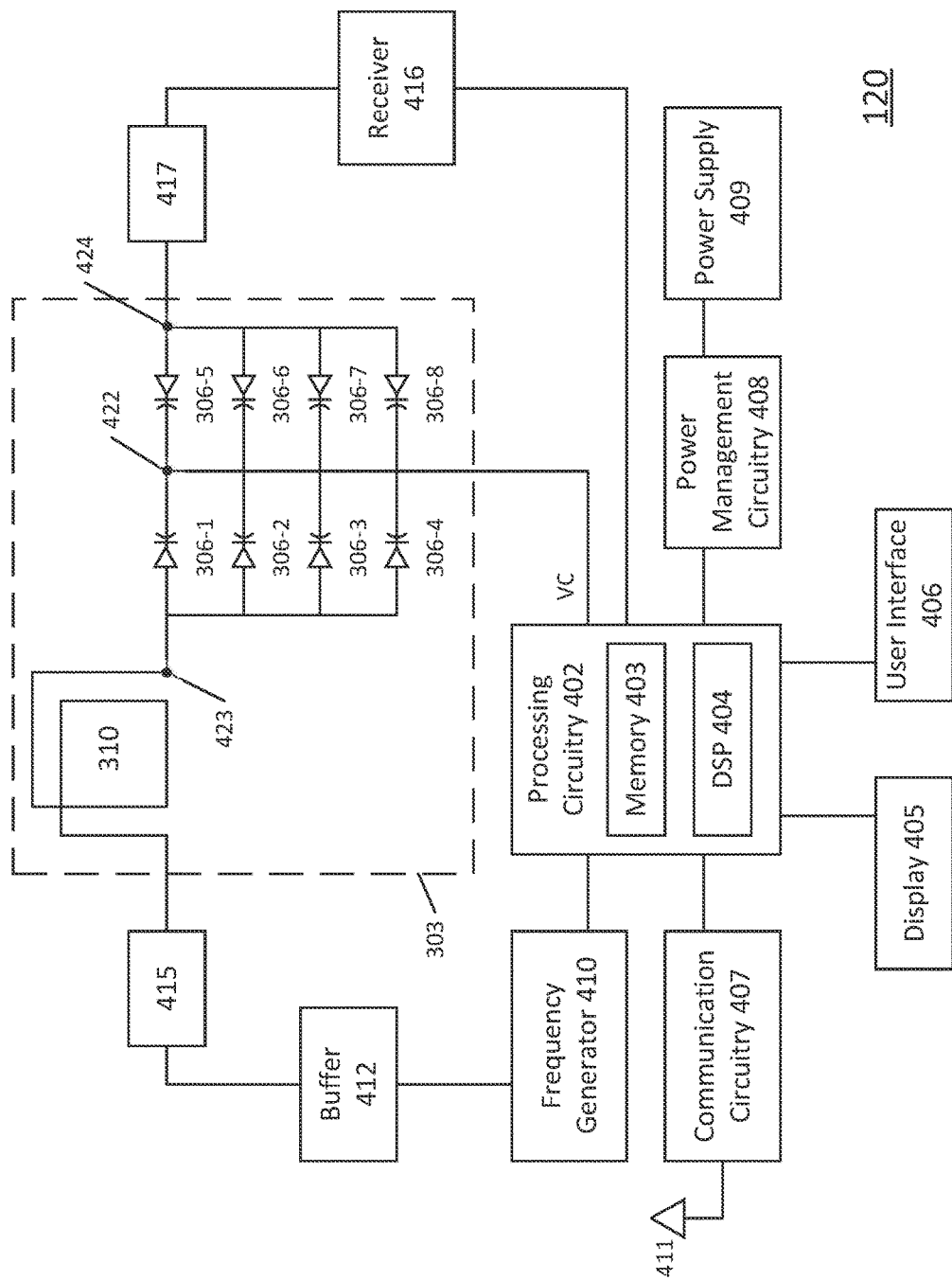
FIG. 4 is a block diagram depicting an example embodiment of a reader device.

FIG. 4 is a block diagram depicting an example embodiment of reader device 120 configured to act as an interrogator of circuit 108. Reader device 120 can be a dedicated reader device (configured for communication other than using mobile telephony) or can be or can include a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN). Reader device 120 can be configured as a modular attachment to a mobile telephone that can, e.g., plug into a wired port of the mobile telephone or can be in communication with the telephone via a wireless connection (e.g., Bluetooth, Wi-Fi, etc.) either directly or indirectly through a relay device. Such a configuration can allow a commercially available mobile telephone to be converted into a device capable of interrogating circuit 108. Reader device 120 can also be configured as a mobile smart wearable electronics assembly, such as an optical assembly that is worn over or adjacent to the user's eye (e.g., a smart glass or smart glasses, such as Google glasses) or devices that are worn around or in the proximity of the user's wrist (e.g., a watch, etc.), neck (e.g., a necklace, etc.), head (e.g., a headband, hat, etc.), chest, or the like.

Here, reader 120 includes processing circuitry 402 with memory 403, optional RF communication circuitry 407 and antenna 411, display 405, user interface 406, power management circuitry 408, power supply 409, frequency generator 410, buffer 412, variable impedance circuit 303, matching circuitry 415 and 417, receiver 416, and antenna 310. FIG. 4 is an abbreviated representation of the hardware and functionality that can reside within reader 120 and those of ordinary skill in the art will readily recognize that other hardware and functionality (e.g., codecs, drivers, glue logic, clocks) can also be included. Some connections between the components of reader device 120 are shown to facilitate understanding of the operation of the circuitry, however reader device 120 will typically have a volume of interconnections too numerous for depiction here and thus a number of interconnections are omitted for clarity.

Processing circuitry 402 can include one or more processors, microprocessors, controllers, and/or microcontrollers, each of which can be a discrete chip or distributed amongst (and a portion of) a number of different chips. Processing circuitry 402 can include digital signal processor 404, which can be implemented in hardware and/or software of processing circuitry 402. In some embodiments, DSP 404 is a discrete semiconductor chip. Processing circuitry 402 can be communicatively coupled with the other components of FIG. 4. Processing circuitry 402 can execute software instructions stored on memory 403 that cause processing circuitry 402 to take a host of different actions and control the other components in reader 120.

Processing circuitry 402 can be coupled with variable impedance circuit 303 at node 422. In this embodiment, variable impedance circuit 303 includes a bank of eight varactor diodes 306-1 through 306-8, each having their cathodes coupled with node 422. The anodes of diodes 306-1 through 306-4 are coupled with node 423 and the anodes of diodes 306-5 through 306-8 are coupled with node 424. Other arrangements of varactor diodes 306 can also be used. Processing circuitry 402 can control the adjustable control voltage (VC), and can include circuitry for outputting VC to node 422 (with power supply 409 acting as the DC source 302 of FIG. 3A) to control the capacitance of diodes 306. Inductor 310 is in the form of a loop antenna 310 that provides the inductance (or substantially all inductance) of circuit 303. As with the embodiment of FIG. 3A, one or more other resistive, capacitive, and/or inductive components can be included, but are not shown here for clarity.

Frequency generator 410 includes circuitry that generates the sweeping RF frequency applied to antenna 310. RC or LC oscillator circuits combined with crystal controlled phase locked loop (PLL) circuits can be used to generate the sweeping RF frequency. This sweeping RF frequency can be used for detection of circuit 108's resonance frequency. The output from frequency generator 410 can be passed through a buffer or gain circuit 412 that can adjust the gain of the output signal, which is then passed through a matching circuit 415 for matching impedance. The RF frequency signal is then propagated or transmitted from antenna 310, which in this embodiment is configured as a loop antenna. Loop antenna 310 can have one or more circular loops, polygonal loops, or combinations thereof. Other antenna configurations can also be used.

A second matching circuit 417 is located between node 424 and a receiver 416. Receiver 416 can capture the signal received at antenna 310 and output the signal to processing circuitry 402, which can then use DSP 404 to analyze whether the resonance frequency of circuit 108 has been detected. Example embodiments of detecting the resonance frequency are described in more detail below.

Processing circuitry 402 can also perform other software and/or hardware routines. For example, processing circuitry 402 can interface with communication circuitry 407 and perform analog-to-digital conversions, encoding and decoding, other digital signal processing and other functions that facilitate the conversion of voice, video, and data signals into a format (e.g., in-phase and quadrature) suitable for provision to communication circuitry 407, and can cause communication circuitry 407 to transmit the RF signals wirelessly over links 141 and/or 142.

Communication circuitry 407 can be implemented as one or more chips and/or components (e.g., transmitter, receiver, transceiver, and/or other communication circuitry) that perform wireless communications over links 141 and/or 142 under the appropriate protocol (e.g., Wi-Fi, Bluetooth, Bluetooth Low Energy, Near Field Communication (NFC), Radio Frequency Identification (RFID), proprietary protocols, and others. One or more other antennas 411 can be included with communication circuitry 407 as needed to operate with the various protocols and circuits. In some embodiments, communication circuitry 407 can share antenna 310 for transmission over links 140, 141, and/or 142. Processing circuitry 402 can also interface with communication circuitry 407 to perform the reverse functions necessary to receive a wireless transmission and convert it into digital data, voice, and video. RF communication circuitry 407 can include a transmitter and a receiver (e.g., integrated as a transceiver) and associated encoder logic. Reader 120 can also include communication circuitry and interfaces for wired communication (e.g., a USB port, etc.) as well as circuitry for determining the geographic position of reader device 120 (e.g., global positioning system (GPS) hardware).

Processing circuitry 402 can also be adapted to execute the operating system and any software applications that reside on reader device 120, process video and graphics, and perform those other functions not related to the processing of communications transmitted and received. Any number of applications (also known as "user interface applications") can be executed by processing circuitry 402 on a dedicated or mobile phone reader device 120 at any one time, and may include one or more applications that are related to a diabetes monitoring regime, in addition to the other commonly used applications, e.g., smart phone apps that are unrelated to such a regime like email, calendar, weather, sports, games, etc.

Memory 403 can be shared by one or more of the various functional units present within reader device 120, or can be distributed amongst two or more of them (e.g., as separate memories present within different chips). Memory 403 can also be a separate chip of its own. Memory 403 is non-transitory, and can be volatile (e.g., RAM, etc.) and/or non-volatile memory (e.g., ROM, flash memory, F-RAM, etc.).

Power supply 409 can include one or more batteries, which can be rechargeable or single-use disposable batteries. Power management circuitry 408 can regulate battery charging and power supply monitoring, boost power, perform DC conversions, and the like.

Display 405 can be a non-interactive display or touchscreen display, and can output information to the user and/or accept an input from the user. One or more optional user interface (UI) components 406 can be present, such as one or more of a button, actuator, touch sensitive switch, capacitive switch, pressure sensitive switch, jog wheel or the like, to input data, commands, or otherwise control the operation of reader device 120. In certain embodiments, display 405 and UI component 406 may be integrated into a single component, for example, where the display can detect the presence and location of a physical contact touch upon the display, such as a touch screen user interface. In certain embodiments, UI component 406 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals.

Reader device 120 may also include an integrated or attachable in vitro glucose meter, including an in vitro test strip port (not shown) to receive an in vitro glucose test strip for performing in vitro blood glucose measurements.

Reader device 120 can display the measured biometric data wirelessly received from OBD 102 and can also be configured to output alarms, alert notifications, glucose values, etc., which may be visual, audible, tactile, or any combination thereof. Further details and other display embodiments can be found in, e.g., U.S. Publ. No. 2011/0193704, which is incorporated herein by reference in its entirety for all purposes.

Reader device 120 can be integrated with a drug (e.g., insulin, etc.) delivery device such that they, e.g., share a common housing, or can be combined with a drug delivery device, e.g., such that one of the two devices is plugged into the other or wirelessly linked to the other. Examples of such drug delivery devices can include medication pumps having a cannula that remains in the body to allow infusion over a multi-hour or multi-day period (e.g., wearable pumps for the delivery of basal and bolus insulin). Reader device 120, when combined with a medication pump, can include a reservoir to store the drug, a pump connectable to transfer tubing, and an infusion cannula. The pump can force the drug from the reservoir, through the tubing and into the diabetic's body by way of the cannula inserted therein. Other examples of drug delivery devices that can be included with (or integrated with) reader device 120 include portable injection devices that pierce the skin only for each delivery and are subsequently removed (e.g., insulin pens). A reader device 120, when combined with a portable injection device, can include an injection needle, a cartridge for carrying the drug, an interface for controlling the amount of drug to be delivered, and an actuator to cause injection to occur. The device can be used repeatedly until the drug is exhausted, at which point the combined device can be discarded, or the cartridge can be replaced with a new one, at which point the combined device can be reused repeatedly. The needle can be replaced after each injection.

The combined device can function as part of a closed-loop system (e.g., an artificial pancreas system requiring no user intervention to operate) or semi-closed loop system (e.g., an insulin loop system requiring seldom user intervention to operate, such as to confirm changes in dose). For example, the diabetic's analyte level can be monitored in a repeated automatic fashion by interrogation of OBD 102, and the appropriate drug dosage to control the diabetic's analyte level can be automatically determined and subsequently delivered to the diabetic's body. Software instructions for controlling the pump and the amount of insulin delivered can be stored in the memory of reader device 120 and executed by processing circuitry 402. These instructions can also cause calculation of drug delivery amounts and durations (e.g., a bolus infusion and/or a basal infusion profile) based on the analyte level measurements obtained from OBD 102.

Example Embodiments of Resonance Frequency Detection

Figure 5A:
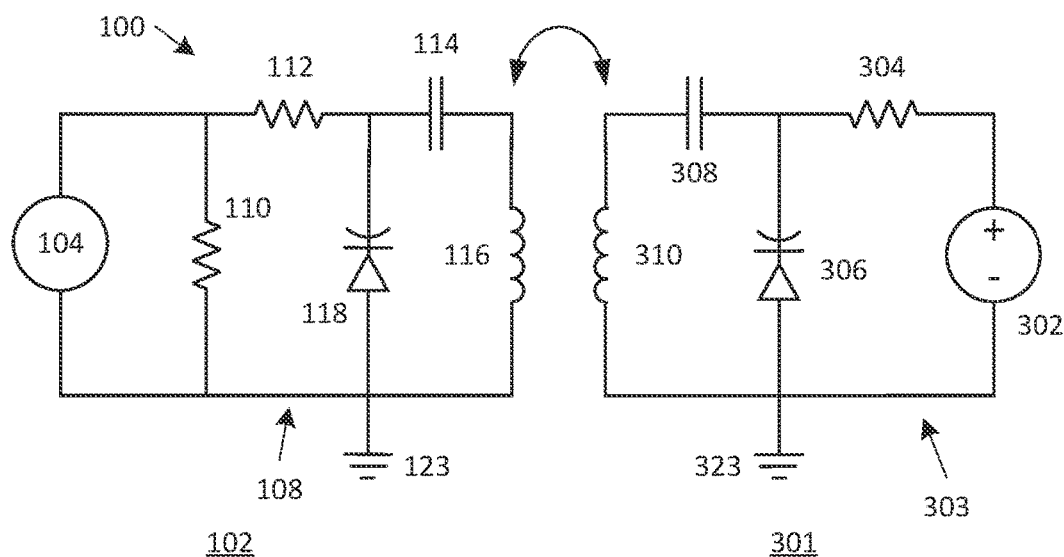
FIG. 5A is a schematic view depicting an example embodiment where of an interrogating circuit in close proximity and inductively coupled to a variable frequency circuit of an on body device.
Figure 5B:
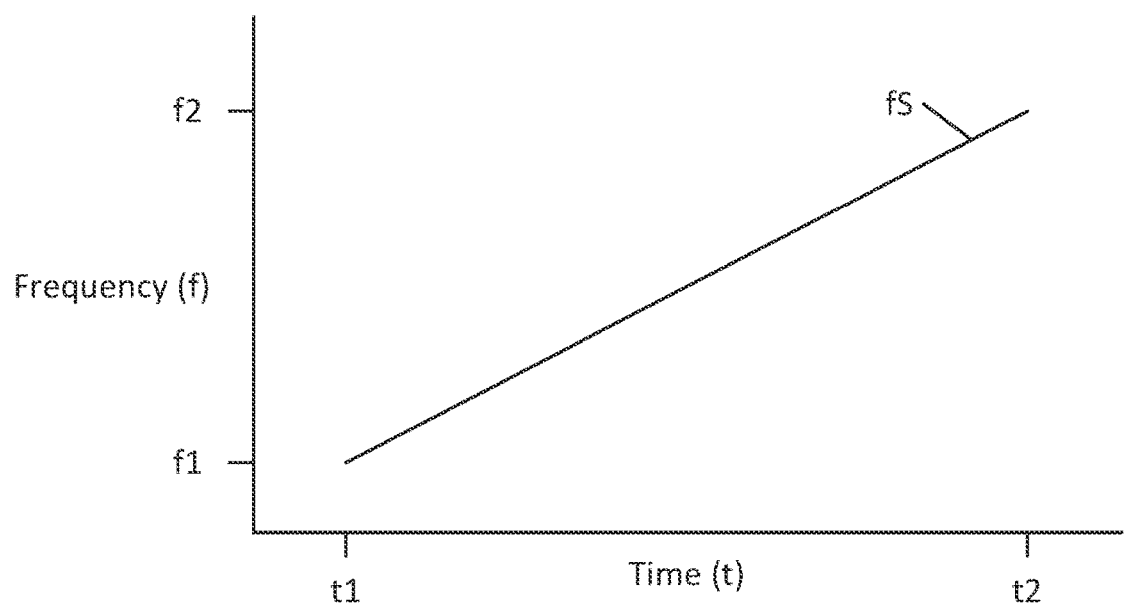
FIG. 5B is a plot of frequency versus time depicting an example of frequencies produced by a frequency generator for transmittal from a reader device.

One example embodiment of a searching process is described with respect to FIGS. 5A-5D. FIG. 5A is a schematic view depicting an example embodiment where interrogating circuit 301 is in close proximity for inductive coupling to variable frequency circuit 108 of OBD 102. FIG. 5B is a plot of frequency versus time depicting an example of frequencies produced by frequency generator 410 for transmittal or propagation from antenna 310 of circuit 303. Here, the sweep frequency (fS) (which can be a discrete frequency or a range of frequencies) increases continuously from a first frequency or range of frequencies (f1) to a second frequency or range of frequencies (f2). In other embodiments, fS can be varied in a stepped fashion, either moving from one adjacent step to the next or by hopping frequencies such that certain frequencies are skipped.

Figure 5C:
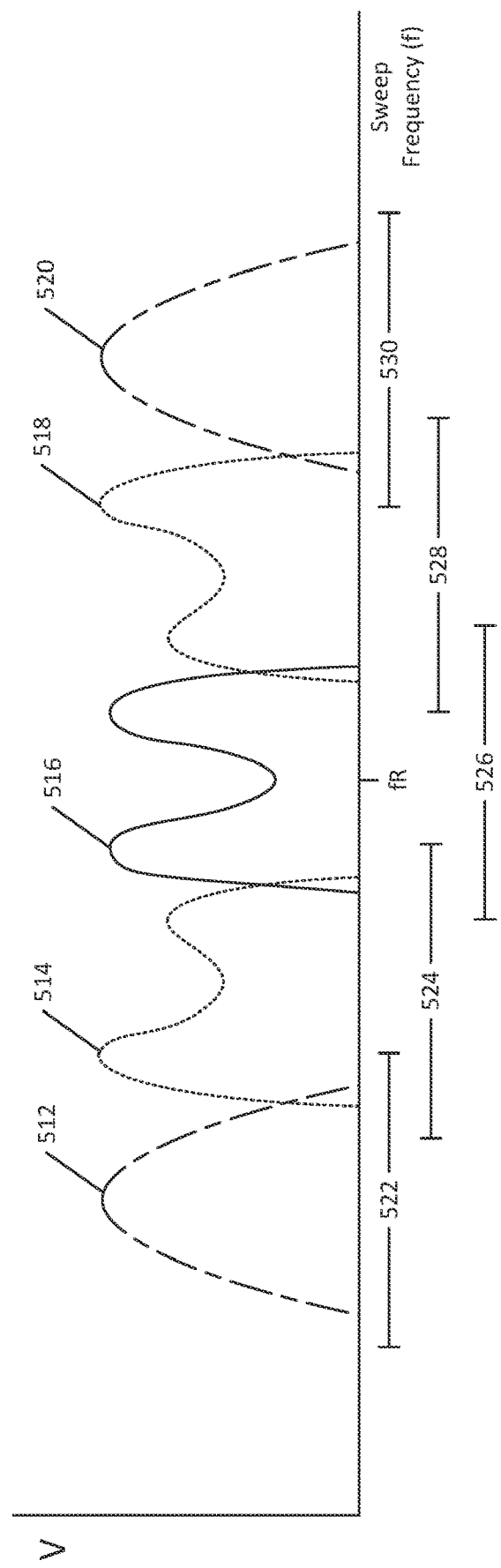
FIG. 5C is a plot of voltage versus frequency with various examples of frequency responses captured by a reader device.

FIG. 5C is a plot of voltage (V) versus frequency (f) with various examples of frequency responses 512-520 captured by receiver 416 of reader 120. Reader 120 can be programmed to detect the resonance frequency of circuit 108 by varying both the sweep frequency (fS) and the control voltage (VC). Variation of the control voltage changes the impedance of circuit 303 and varies range of frequencies that receiver 416 captures. For example, a first control voltage can result is receipt of frequencies in the range fA-fB, where a second control voltage can result in receipt of frequencies fC-fD. These frequency ranges can be overlapping or non-overlapping and can be referred to as receiving windows. FIG. 5C depicts examples of five responses captured with receiver 416 tuned, at different times, to five different receiving windows: response 512 in receiving window 522, response 514 in receiving window 524, response 516 in receiving window 526, response 518 in receiving window 528, response 520 in receiving window 530. Each receiving window 522-530 can be overlapping and can vary in size or width (i.e., the range of frequencies within the window). Receiving window width can be determined by the measurement resolution of the system. Processor 402 can be programmed to cause generation of a particular range of sweep frequencies for each window. The size of each window can be the same or different depending on the position of the receiving window within the overall frequency band in which the system is operating.

With receiver 416 tuned to a particular receiving window, a range of transmission frequencies can be varied or swept (e.g., such as the example sweep from f1-f2 shown in FIG. 5B). As the transmission frequencies are swept, one or more frequency responses (e.g., responses 512-520) will be generated sequentially and captured by receiver 416 for each receiving window. Receiver 416 can output the captured response or data indicative of the response for analysis by DSP 404. The size and shape of the frequency responses will vary depending on the degree of inductive coupling that is present between circuits 108 and 303.

A low degree of inductive coupling can result in a single peak such as depicted in responses 512 and 520, which are relatively far from the resonance frequency fR of circuit 108. As the receiving window more closely approximates fR, a higher degree of inductive coupling occurs and the response begins to shift from the single peak form to a double peak form like that depicted in responses 514, 516, and 518. This type of behavior is similar to that of a double tuned amplifier, where the response is critically coupled when two peaks begin to form, and the peaks become more pronounced and further apart as the coupling coefficient (k) grows (e.g., an overcoupled state).

Figure 5D:
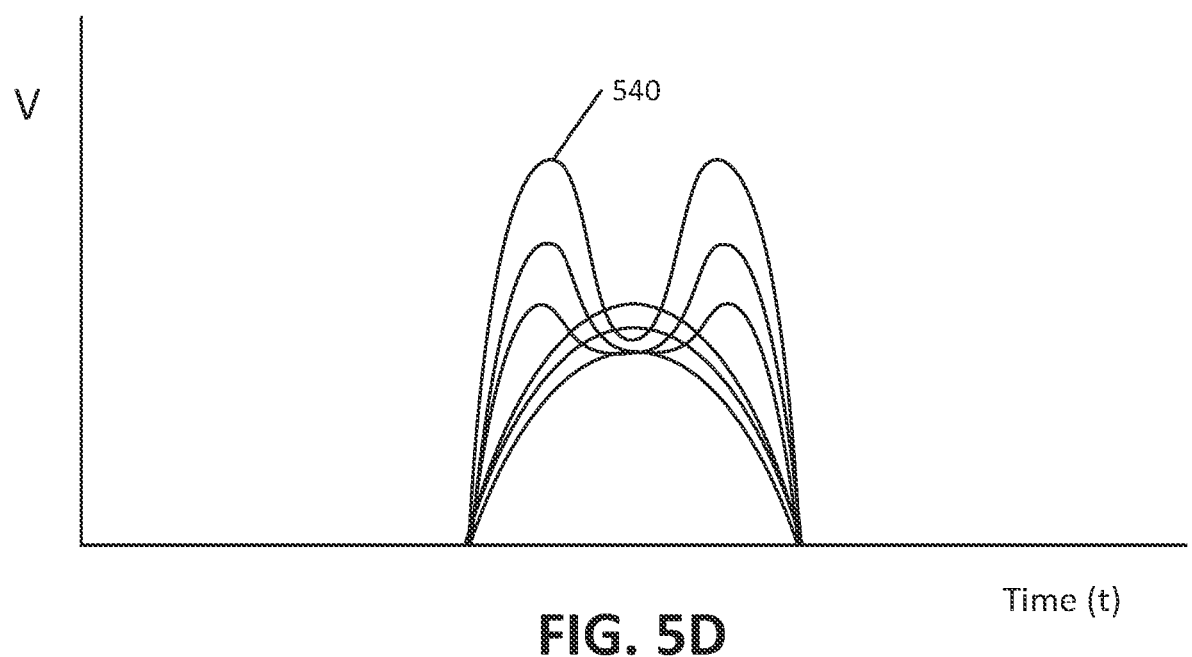
FIG. 5D is a plot of voltage versus time with various examples of responses captured by a reader device.

Response 514 is a double-peak response with peaks at different heights or magnitudes. Here the lower frequency peak has a greater magnitude than the higher frequency peak. Conversely, response 518 is a double-peak response with a reverse shape where the lower frequency peak has a lesser magnitude than the higher frequency peak. Response 516 is a double-peak response where the peaks are of the same or substantially the same height (magnitude), which can be indicative of centering around fR. Reader 120 can, in some embodiments, monitor for and detect the occurrence of the equal height response 516, and use this response to determine fR. FIG. 5D is a plot of voltage versus time depicting examples of the output of receiver 416 overlaid in the time domain. Output signature 540 corresponds to response 516 of FIG. 5C. Once fR is determined, processing circuitry 402 can execute programming to determine the corresponding analyte level of the user, which can then be output to the user on display 405 and/or transmitted to another device via communication circuitry 407.

Figure 6:
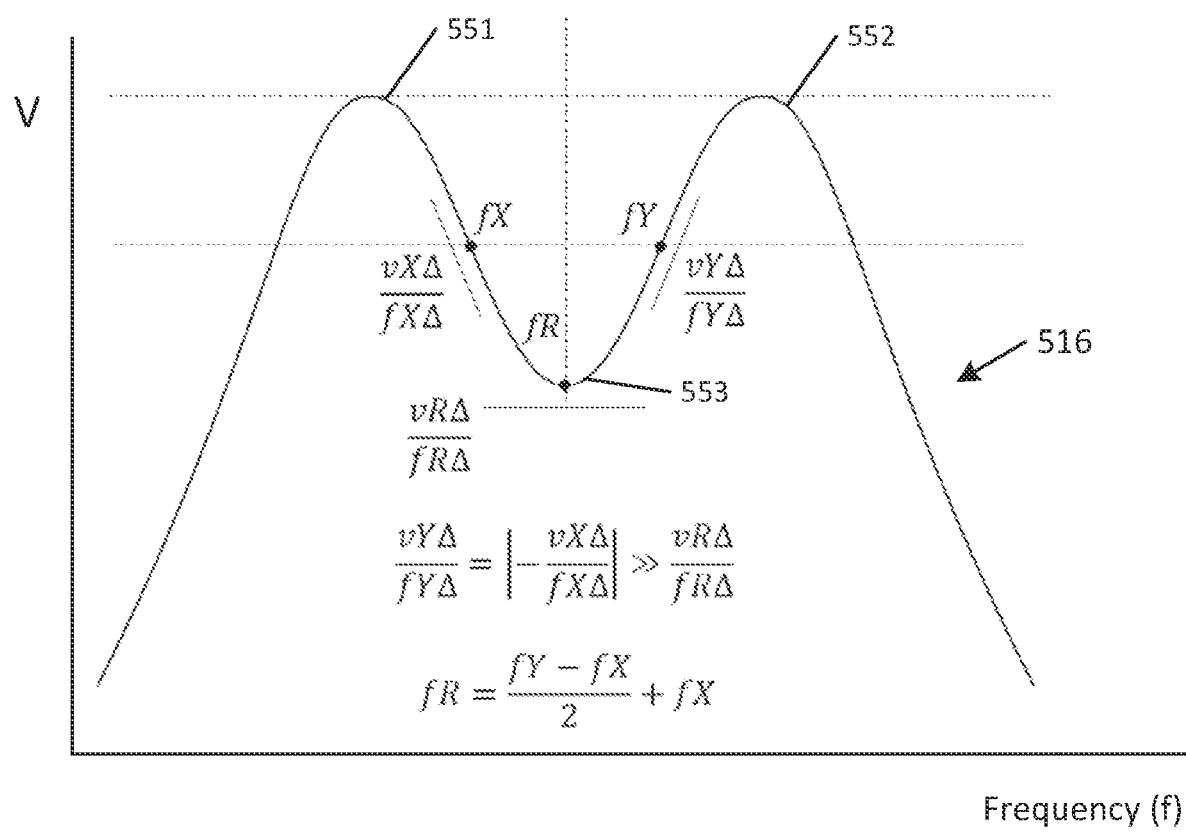
FIG. 6 is a plot of voltage versus frequency with an example of a double peak response suitable for use in determining a resonance frequency of an on body device.

FIG. 6 is a plot of voltage versus frequency with an example of a double peak response 516 suitable for use in determining the resonance (or resonant) frequency (fR) of circuit 108. When peaks 551 and 552 are the same or substantially the same height they will also be symmetric, or substantially symmetric, and a trough 553 (or inverted peak) will be present between them. If a readily identifiable V value for the minimum of trough 553 exists, then that value can be used as the resonance frequency (fR). In some cases, trough 553 may have multiple frequencies at the minimum value (e.g., trough 553 has a flat bottom). To account for this, DSP 404 can divide the distance between the maximum Z value of the two symmetric peaks 551 and 552 and the minimum V value of trough 553 between the peaks. Response 516 will have this V value at four frequencies. The maximum and minimum of the four frequencies can be ignored and the two remaining frequencies (the two middlemost frequencies) fX and fY can be identified. The average of fX and fY is the value half way between them and corresponds (or closely approximates) the resonance frequency fR according to (2) below:

$$fR = \frac{fY - fX}{2} + fX$$

This approach can determine fR with certainty as the slope of response 516 in the regions of fX and fY is significant and thus allows fX and fY to be readily ascertained.

Example Embodiments of Analyte Level Determination

Determination of the corresponding analyte level from the detected resonance frequency can be accomplished in various ways. The following examples make reference to numerical values for ease of description of the underlying concepts. These numerical values are examples only and in no way limit the subject matter to only such values. Actual implementations can and will vary.

Figure 7A:
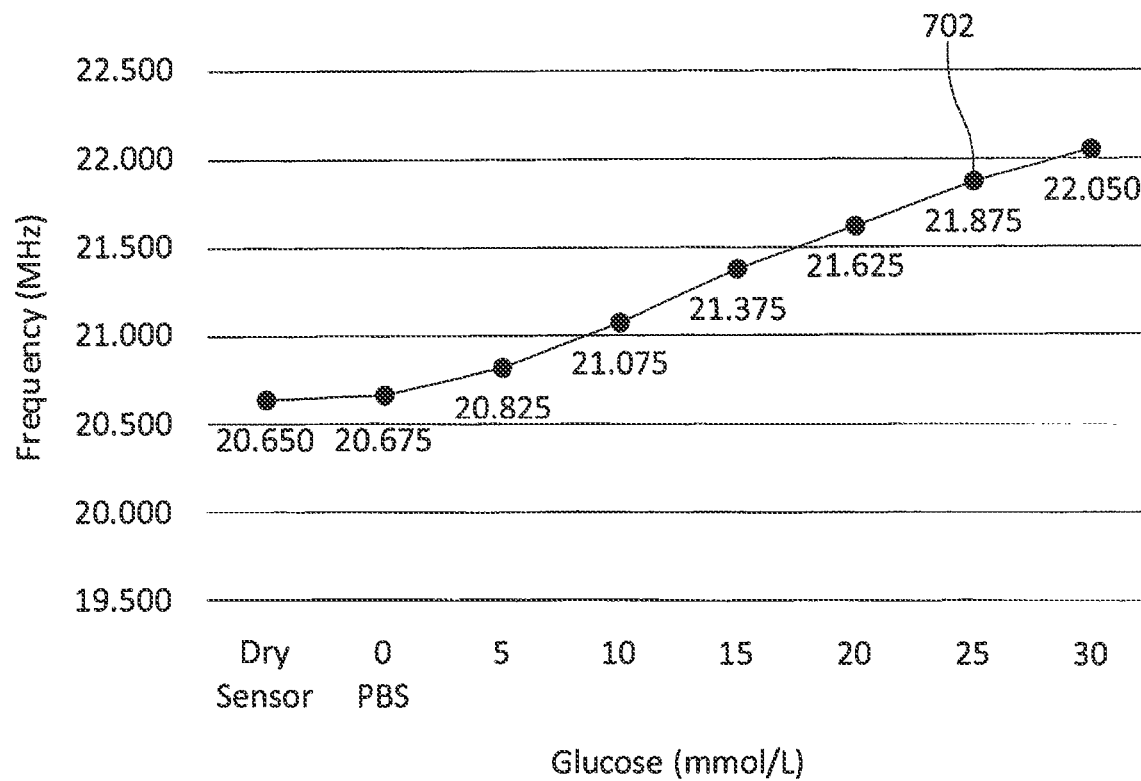
FIG. 7A is an example of a correlation between glucose level and resonance frequency for the embodiment of FIG. 2C.

FIG. 7A is an example of a correlation 702 between glucose level and resonance frequency for the embodiment of FIG. 2C, where the example sensor has a resonance frequency of 20.675 Megahertz (Mhz) at a glucose level of zero mmol/L and a value of 22.050 Mhz at a glucose level of 30 mmol/L.

In some embodiments, correlation 702 can be stored in memory 403 of reader device 120 in the form of a look-up table, array, or other data structure that maps many different resonance frequencies to their corresponding glucose concentrations. Processing circuitry 402 can cross-reference the detected resonance frequency and determine the corresponding glucose concentration. In other embodiments, correlation 702 can be coded in the software instructions executed by processing circuitry 402 in the form of an algorithm. For example, if correlation 702 is linear or substantially linear, the algorithm can be in the form of (fR−b)/s=g, where fR is the measured resonance frequency, b is a predetermined value corresponding to the frequency offset measured at the y-axis intercept, s is a predetermined value of the slope of the linear correlation, and g is the corresponding glucose level. Processing circuitry 402 can determine the glucose concentration by inputting the measured resonance frequency into this formula. Non-linear correlations can utilize more complex polynomial relationships, or can be approximated with different linear relationships for various regions.

Correlation 702, whether in the form of a data structure or algorithm, can be obtained theoretically, experimentally, or a combination thereof. In some embodiments it is desirable to characterize each OBD 102, e.g., during assembly and/or final testing by the manufacturer. Each OBD 102 can be subjected to an in vitro test by exposing sensor 104 to one or more test solutions having various concentrations of analyte (e.g., glucose), while at the same time measuring the resulting resonance frequency. For example, sensor 104 can be tested in solution with zero glucose, and then subjected to one or more additional exposures to solutions having other differing non-zero glucose concentrations. In some embodiments the sensor 104 may only be exposed to test solution once (either zero or non-zero glucose concentration). This process can be used to generate the look-up data structure directly (e.g., if many different glucose concentration tests are performed), or can be used to obtain a subset of correlation points, and a data regression can be performed to fit a linear or non-linear line or curve from which the look-up data structure and/or algorithm (e.g., values for slope and intercept) can be obtained.

In some embodiments, a current can be applied to variable frequency circuit 108 to simulate that which would be applied by sensor 104 ($I_S$) at various glucose concentrations, and the resulting resonance frequency can be detected and correlation 702 generated. In other embodiments, measurements of the resistance, capacitance, and/or inductance of the components of OBD 102 can be obtained and used algorithmically determine the frequency correlation. For example, the impedance (e.g., capacitance) to voltage correlation of the one or more components 118 can be measured or characterized and used to determine the frequency correlation. Such approaches permit characterization of circuit 108 without actually exposing sensor 104 to glucose solution during the testing process. In such cases the resonance frequency when sensor 104 is dry (as described below) can be used for correlation of the sensor 104 at a zero analyte level. In other embodiments, sensor 104 to can be tested when dry and then one or more times in test solution (e.g., with zero or non-zero analyte levels). This process can be used to generate the look-up data structure directly (e.g., if many different current tests are performed), or can be used to obtain a subset of correlation points, and a data regression can be performed to fit a linear or non-linear line or curve from which the look-up data structure and/or algorithm (e.g., values for slope and intercept) can be obtained.

In embodiments where sensor 104 is not exposed to test solution, a second correlation can be utilized to convert sensor current (IS) to the glucose concentration (or to apply calibration to adjust the determined glucose concentration to a calibrated value). The process of correlating sensor measurements to analyte values is well known to those of ordinary skill in the art, and can be accomplished by use of look-up data structures and/or algorithms with or without sensor calibration values.

In still other embodiments, a universal correlation can be used that applies to all OBDs 102 and readers 120. For example, in systems 100 where inter-device impedance variations are minimal, a universal correlation can be derived and used by all devices in determining analyte level from a measured resonance frequency.

Figure 7B:
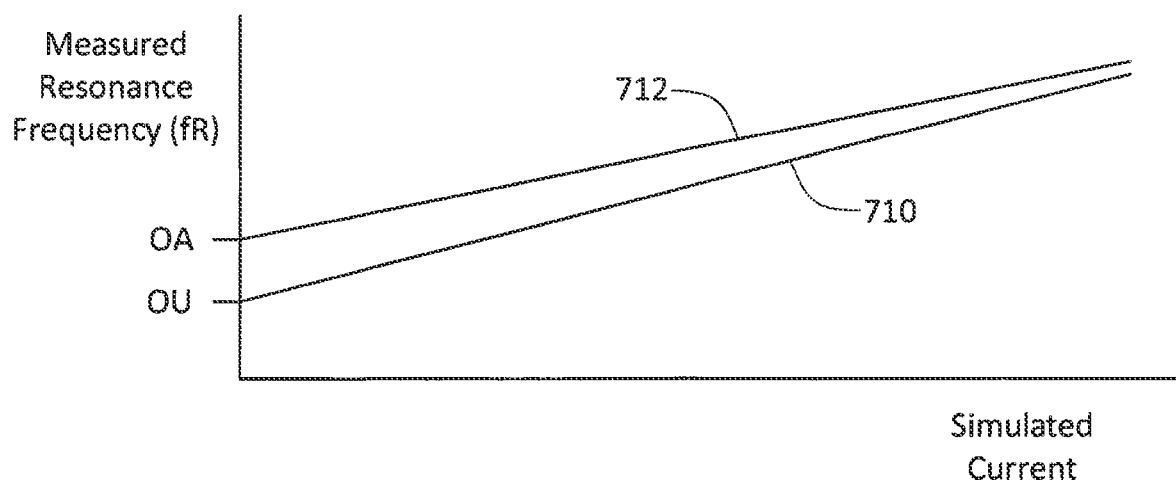
FIG. 7B is a plot of simulated sensor current versus resonance frequency.

In some embodiments, a universal correlation can be used and modified by calibration values specific to a particular OBD 102. FIG. 7B is a plot of simulated sensor current versus resonance frequency. A universal linear correlation is given by trace 710, and a linear correlation measured for a particular OBD 102 is given by trace 712. The offset for universal correlation 710 (OU) differs from that of the actual measured correlation 712 (OA), and the slope differs for both correlations 710 and 712 as well. These differences can be quantified and stored as frequency calibration values (offset difference and/or slope difference) particular to that OBD 102. Reader device 120 can utilize these frequency calibration values to adjust the determined resonance frequency measurement, or inferred sensor measurement (e.g., $I_S$) accordingly.

Correlation 702 and/or frequency calibration values specific to a particular OBD 102 (OBD-specific data) can be made available to reader device 120 (or other device) in a number of different ways. The OBD-specific data can be transferred to reader device 120 in the form of the actual value(s) or in the form of a code that corresponds to the actual value(s). The code can be translated to the corresponding value by use of a lookup data structure or algorithm (e.g., stored in memory 403 of reader 120). If OBD 102 includes non-transitory non-volatile memory, then the OBD-specific data can be stored in that memory and communicated to reader device over link 140 as part of any communication between OBD 102 and reader device 120. For example, upon activation of OBD 102 by reader device 120, or in the process of detecting the resonance frequency, or immediately after the resonance frequency is detected, OBD 102 can provide the OBD-specific data (either automatically or in response to a specific request for such).

In other embodiments, the OBD-specific data can instead be printed on the packaging (or packaging inserts) of OBD 102 or directly on the housing of OBD 102. In these embodiments, the user can read the OBD-specific data and manually input it into reader 120, or alternatively use reader 120 to automatically obtain the OBD-specific data from the packaging or housing for OBD 102 (e.g., by optically scanning a barcode). In other embodiments, the calibration code can be readable from a calibration code module that can be plugged into reader 120. In still other embodiments, an NFC scannable device (e.g., a tag) can be placed on the packaging, or on or within OBD 102, and that NFC scannable device can be scanned by reader 120 to obtain the calibration code. The NFC scannable device can also include a unique sensor ID to identify the sensor and start a wear duration clock (e.g., if the sensor has a limited lifespan) so that reader 120 will know when the sensor expires.

In other embodiments, the OBD-specific data can be uploaded to, e.g., trusted computer system 180, and then subsequently retrieved or downloaded by reader device 120 over network 190. In these embodiments, reader device 120 can obtain an identifier for OBD 102 (either by scanning OBD 102 or by manually or automatically obtaining the identifier, etc.) and transmit it to trusted computer system 180 which can then locate the OBD-specific data and communicate it back to reader device 120 over a network 190.

All of the foregoing embodiments pertaining to characterization of circuitry can likewise be applied to reader 120, such as circuit 303 of reader 120. For example, if component variation causes a particular reader 120 to measure a resonance frequency to be slightly higher than the actual value, such can be quantified through characterization (e.g., testing) of reader 120. Such information (e.g., in the form of a +/−frequency offset and/or slope) can be stored in memory 403 of reader 120 and used to calibrate reader 120 to more accurately determine the measured resonance frequency and/or analyte level.

Referring back to the embodiment of FIG. 2C, a process of determining the resonance frequencies with non-limiting example values is provided. In this example resistor 110 is 5 Megaohms (MΩ) and inductor 116 is 800 nanoHenries (nH). The value for resistor 112 is between 2 and 4 MΩ (e.g., 3 MΩ in this example) and is used to block the AC signal from circuit 108 to resistor 110. The DC voltage at nodes 120 and 121 can be assumed to be the same with negligible current through resistor 112. The total capacitance of the varactor diodes 118-1 and 118-2 with no current ($I_S$) is 74.25 picoFarads (pF) (when sensor 104 is dry) and 74.07 pF (when sensor 104 is wet). Generally, a small amount of AC leakage exists when sensor 104 is wet, and no AC leakage exists when sensor 104 is dry, which accounts for the difference in capacitance values between the two states, although in both cases there is no DC current output from sensor 104. At a glucose concentration of 30 mmol/L, the total capacitance is 65.12 pF. A current of 30 nA will flow through the 5 MΩ resistor and place a voltage of 150 mV across diode 118. In this embodiment, sensor 104 has an output range of 0-30 nanoAmps (nA) for a glucose range of 0-30 mmol/L with a 1:1 correlation. Using equation (1) described with respect to FIG. 2A, circuit 108 will have a resonance frequency of 20.675 MHz (wet) with no current and 22.050 MHz with 30 nA of current. All of the values stated here are merely examples and those of ordinary skill in the art will understand that such values will vary depending on the implementation. Resonance frequencies for other sensor currents can also be determined based on FIG. 7A.

Determining a glucose result on reader 120 from matching the resonance frequency can be the reverse process. For example, reader circuit 303 can be calibrated like sensor circuit 108 (e.g., with a slope and/or intercept) to define the correlation so that the change in capacitance from the matched frequency to the no load frequency can be used to determine the equivalent applied voltage to varactor diode 118. The voltage divided by the resistance of resistor 110 gives the equivalent current (Is) from sensor 104. The glucose value can then be algorithmically calculated to compensate for the sensor response.

Example Embodiments of Frequency Searching

Figure 8A:
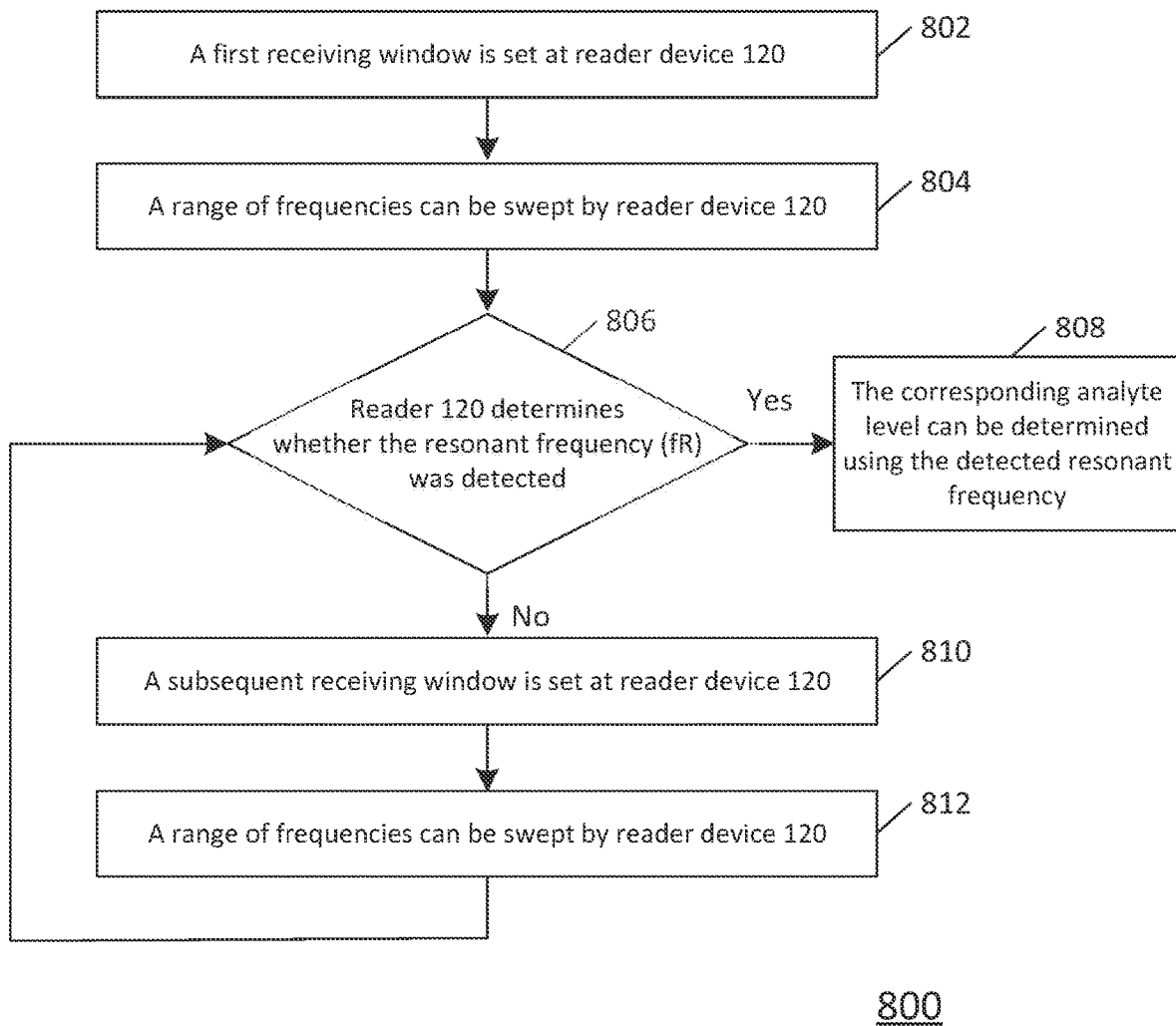
FIGS. 8A-8B are flow diagrams depicting example embodiments of methods of scanning an on body device.

Various techniques can be employed to determine the resonance frequency. The process of holding reader device 120 in proximity with OBD 102 and searching for the resonance frequency can be referred to as a scan. FIG. 8A is a flow diagram depicting an example embodiment of a method of scanning 800. At 802, a first receiving window is set, e.g., by processing circuitry 402 causing application of a constant voltage (VC) to variable impedance circuit 303 of reader device 120. At 804, a range of frequencies fS can be propagated or swept by reader device 120 using frequency generator 410, and the response can be captured (e.g., with receiver 416). At 806, it is determined by processing circuitry 402 whether the resonance frequency (fR) was detected in the captured response. If so, then at 808 processing circuitry 402 of reader device 120 can use the detected fR to determine the corresponding analyte level (e.g., by use of a proprietary algorithm that applies the correlation value, or otherwise), which can then be output to the user (e.g., on display 405). If fR is not detected, then at 810 the constant voltage (VC) can be adjusted to set a new receiving window and, at 812, a range of frequencies fS can be swept by reader device 120. This range of frequencies can be the same or different from those frequencies swept at 804, as will be described below. The method can then revert to the determination at 806, and the process can repeat until the resonance frequency fR is detected. Although not shown, if all receiving windows are cycled through without detecting the resonance frequency fR, or the method otherwise fails, then processing circuitry 402 can generate an indication of error or failure that can then be output to the user (e.g., on display 405).

Figure 8B:
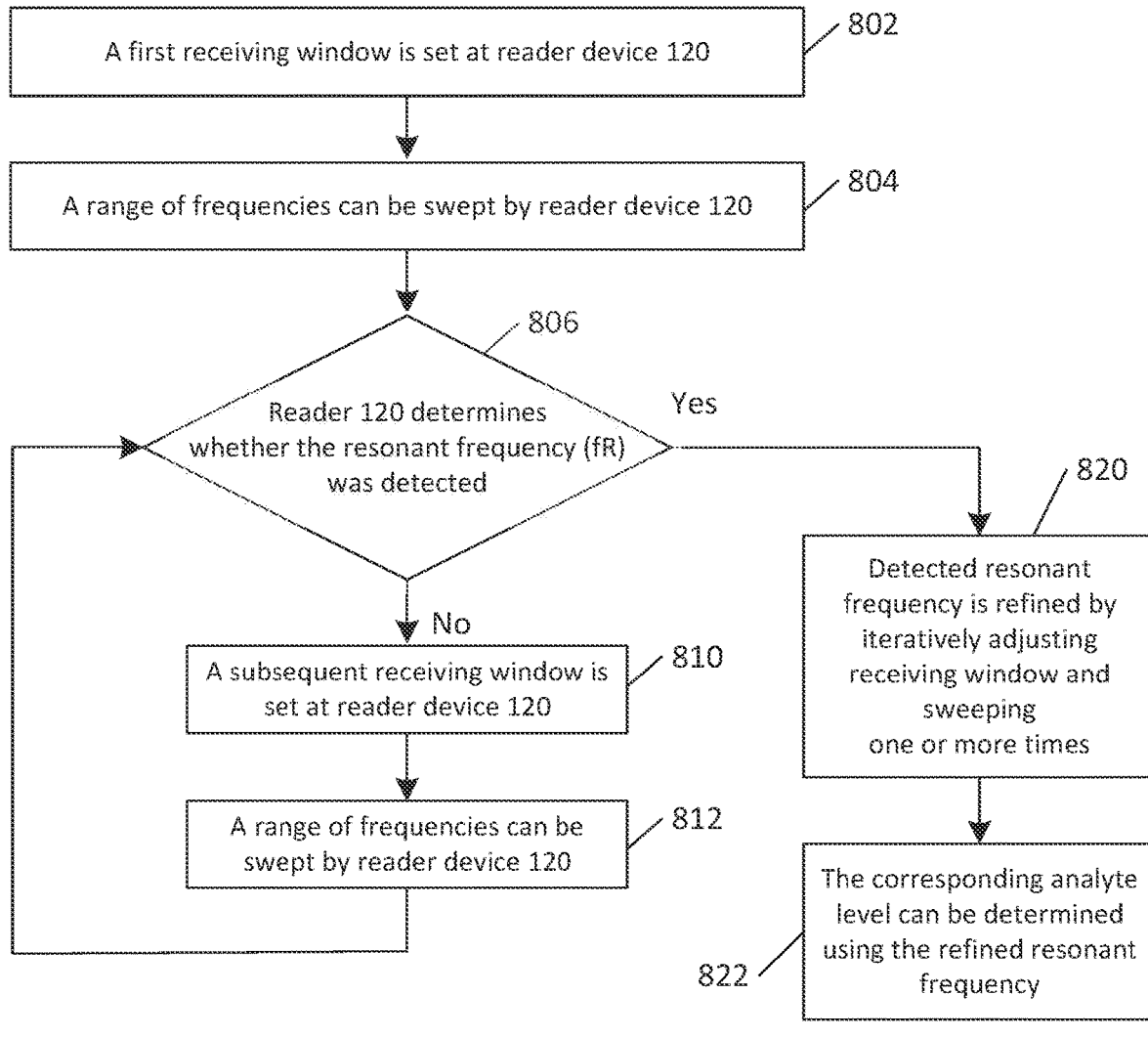

FIG. 8B is a flow diagram depicting another example embodiment of a method 800 of scanning. In this embodiment, if the resonance frequency fR is detected at 806, then the value of the resonance frequency can be more precisely determined by an optional refined detection 820. For example, once fR is detected at 806 using a particular receiving window and VC (e.g., 2.4 volts), the VC corresponding to that receiving window can be adjusted by increments less than those used to index between receiving windows. For example, if the first round of indexing occurred at VC increments of 0.1 volts, then upon detecting fR, VC can be adjusted by smaller increments (e.g., 0.01 volts), each time sweeping at least the corresponding fS frequencies to more accurately determine or refine the value of fR. If the detected resonance frequency fR is determined to be on the lower frequency side of the receiving window, then VC can be lowered in smaller incremental steps until fR is fully matched. Once fR is identified, reader device 120 can determine the corresponding analyte level at 822 and then output to the user if desired.

Three sets of example embodiments of setting the receiving window and sweeping frequencies will now be described, each of which can be implemented with method 800 of FIGS. 8A-8B. These embodiments will be described with reference to the example frequency vs time plots of FIGS. 9A-9G, where the frequencies being swept and the receiving window are indicated by reference numerals 902 and 904, respectively. These embodiments are merely examples and are not exhaustive of every manner of performing a scan. While these embodiments are described with receiving windows that are adjacent but non-overlapping, those of ordinary skill in the art will understand that each adjacent receiving window can also partially overlap. Also, these embodiments are described with sweeps that increase in frequency over time (e.g., from fmin to fmax), but these embodiments can be similarly implemented with sweeps that decrease in frequency over time (e.g., from fmax to fmin).

In a first set of embodiments, described with reference to FIGS. 9A-9B, each receiving window 904 has a bandwidth that is less than the overall range of frequencies in which the resonance frequency can be detected (e.g., fmin through fmax). Reader device 120 (e.g., processing circuitry 402) can be programmed to initially sweep the full frequency (fS) range (fmin-fmax) of OBD 102 while a constant VC (e.g., 2.0 volts) is applied to circuit 303 to set a specific receiving window 904 (e.g., fmin-fA). This can entail sweeping fS frequencies outside of receiving window 904. If the resonance frequency (fR) is not detected, processing circuitry 402 can adjust VC (e.g., 2.4 volts) to move or index to a new value and thus a new receiving window 904 (e.g., fA-fB) and, then reader 120 can sweep the full range of fS again. This process can continue iteratively until fR is detected and identified (e.g., a double peak response 516). Although not required, preferably the process is fast enough to occur within a single scan of OBD 102 (e.g., less than 5 or 10 seconds).

Figure 9A:
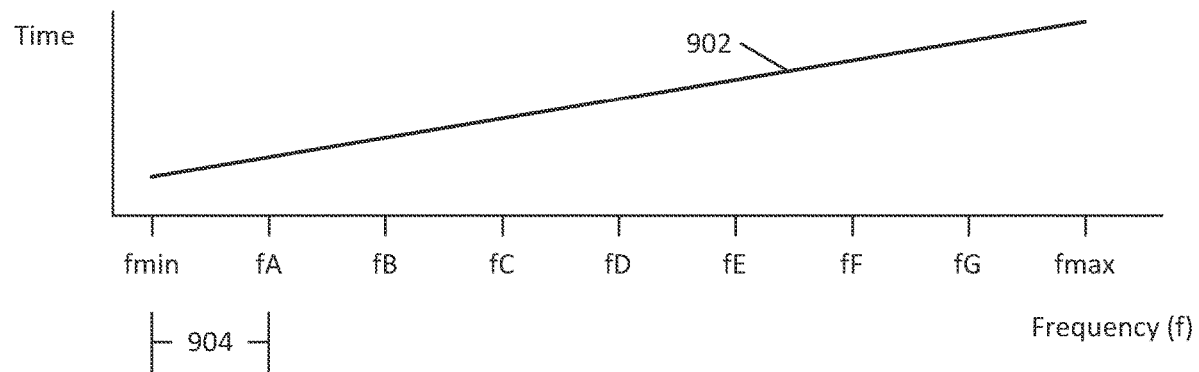
FIGS. 9A-9G are plots of time versus frequency depicting various aspects of example embodiments of scanning an on body device.
Figure 9B:
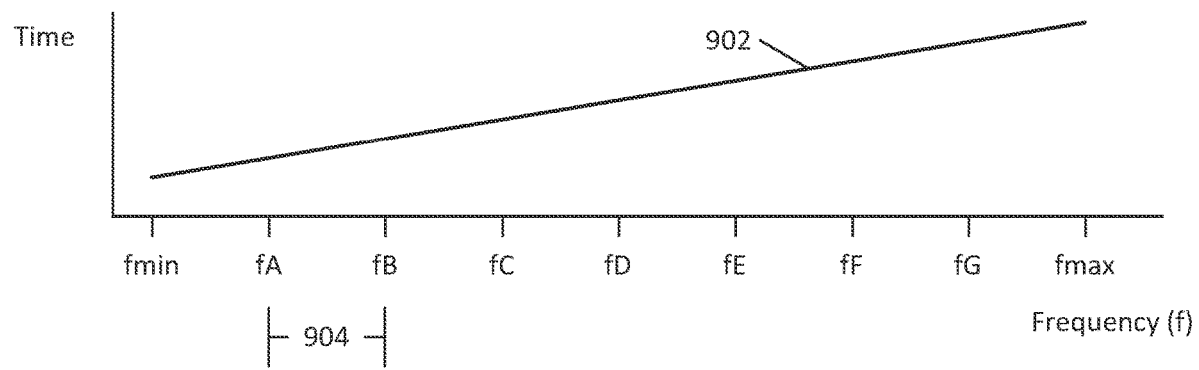
Figure 9C:
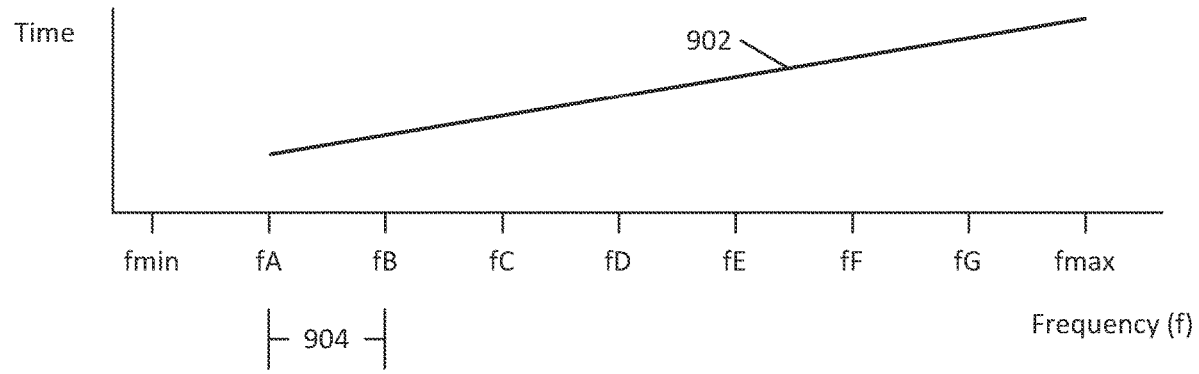
Figure 9D:
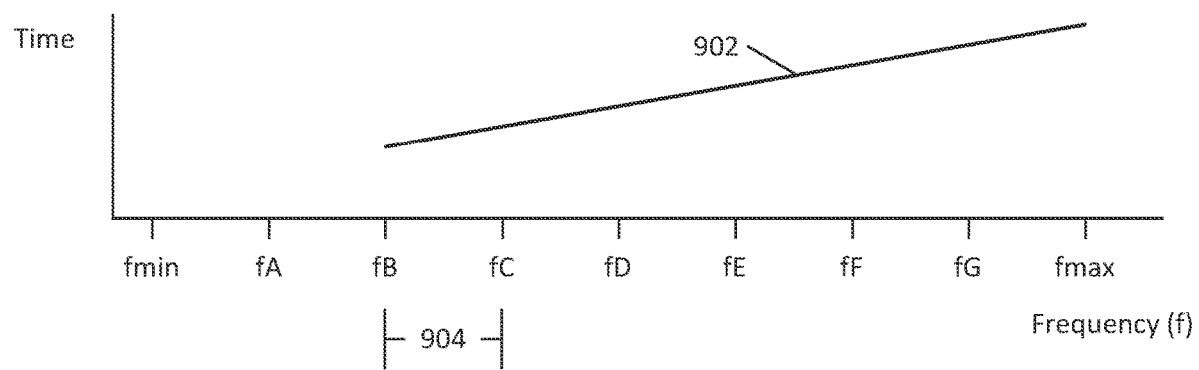
Figure 9E:
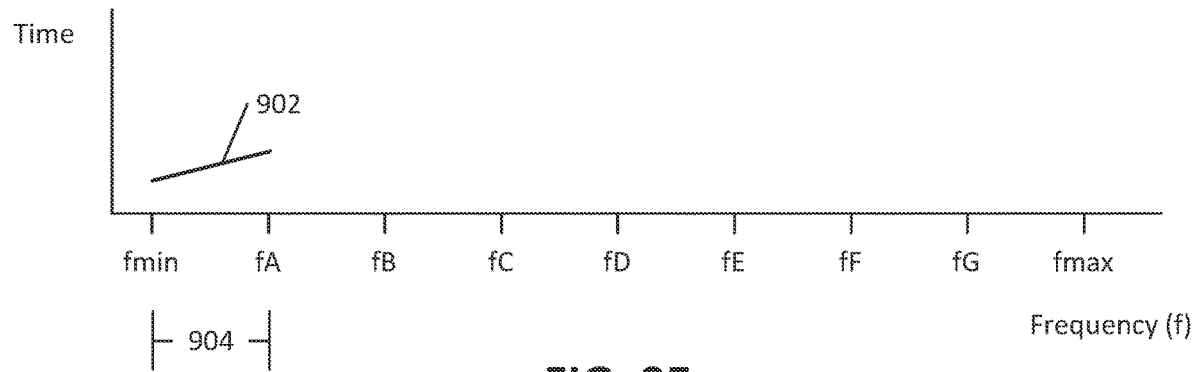
Figure 9F:
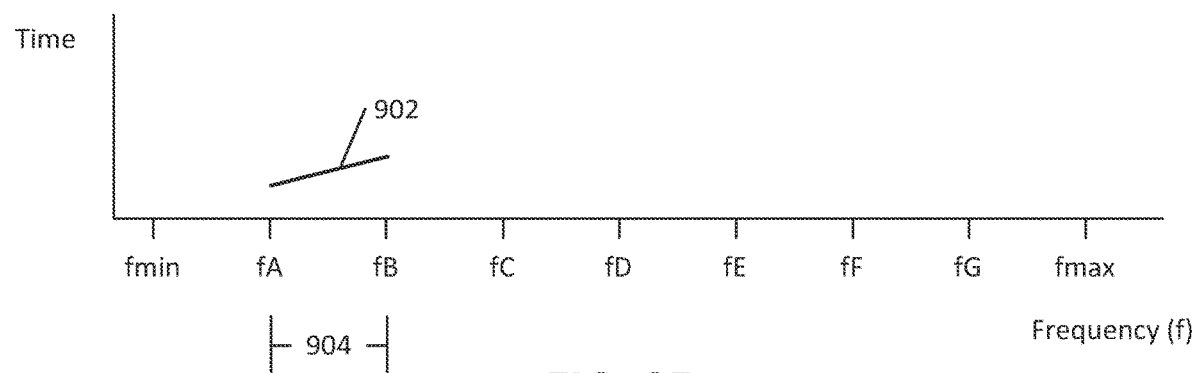
Figure 9G:
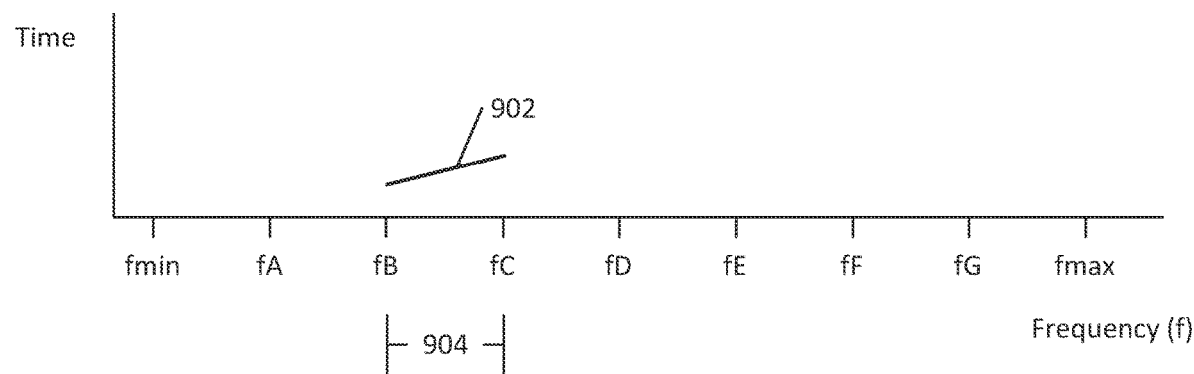

In a second set of embodiments, after a first sweep like that of FIG. 9A, reader 120 can index to a new (second) receiving window 904 (e.g., fB-fC) and sweep a range of fS less than the full range of fS. For example, the second sweep can begin at the lowest frequency in the current receiving window (e.g., fA) and proceed to fmax as depicted in FIG. 9C. The third sweep can then begin at a still higher frequency (e.g., fB) and proceed to fmax as depicted in FIG. 9D. Alternatively, in opposite fashion, each sweep can begin at fmin and proceed to the highest frequency within the active receiving window. In another variation, the sweep frequencies can be commensurate with each receiving window such that each sweep includes only those frequencies within the current receiving window, as depicted in the sequence of FIGS. 9E-9G. For example, if the first receiving window was fmin to fA (FIG. 9E), then upon indexing to a second window at fA-fB, the fS sweep can begin at fA and proceed to fB (FIG. 9F), and then upon indexing to a third window at fB-fC, the fS sweep can begin at fB and proceed to fC (FIG. 9G). Thus, upon indexing, the fS sweep would not repeat frequencies already examined with the prior receiving window. Further, the fS sweep can be stopped once it is determined that the frequencies within the particular receiving window have already been transmitted (e.g., fB is reached). This process can be iteratively repeated until fR is identified. Thus, in some embodiments, a single sweep of fmin to fmax can be performed with the receiving window being indexed each time fS reaches the beginning of the next receiving window.

In a third set of embodiments, each of the first and second set of embodiments can be practiced but reader device 120 can be programmed to use, as the first receiving window, the same receiving window in which fR was detected the last time a scan was performed. Thus, if the measured analyte has not changed significantly the scan time can be reduced. For example, if fR was detected in the fC-fD window during the last scan, then the next scan can begin with VC set to the fC-fD window. In some embodiments, instead of using the receiving window in which fR was last detected, reader device 120 can track the average or median analyte level of the user and start with the receiving window that corresponds to the most recently determined average or median value. Thus, if fR was last detected in the fC-fD window, but the average value indicates the fD-fE window, then the next scan can initiate with the receiving window set to the fD-fE window. In both embodiments if fR is detected then the scan can stop. If not, then the receiving window can be indexed to the receiving windows immediately adjacent to the recently swept window in any desired order. For example, if fR is not detected upon initially sweeping the fD-fE window, then the fC-fD window can be swept next, followed by the fE-fF window, followed by the fB-fC window, and so forth until fR is detected. In some embodiments, processing circuitry 402 can be programmed to center the first receiving window around the last detected fR to optimize the search, and then proceed by indexing receiving windows from there.

While these embodiments utilize a receiving window that is smaller than the overall band of frequencies in which the resonance frequency can exist, other embodiments can utilize a receiving window that is as broad as the overall band of frequencies such that moving the receiving window is not required.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many example embodiments, a method of detecting an analyte sensor measurement is provided, the method including: outputting, by an analyte sensor of a first device, an electrical current or voltage that corresponds to an analyte level of a user, where the analyte sensor is electrically coupled with a circuit having a frequency characteristic adapted to vary according to the electrical current or voltage; wirelessly detecting the frequency characteristic of the circuit with a second device; and determining the analyte level of the user based on the detected frequency characteristic.

In these embodiments, the frequency characteristic can be a resonance frequency. The circuit can have an impedance that varies according to the electrical current or voltage. The circuit can include a component having a capacitance that varies according to the electrical current or voltage. The electrical current or voltage can be applied to the component, and the method can further include: outputting, by the analyte sensor, a varying electrical current or voltage that corresponds to a varying analyte level of a user, where the impedance of the circuit varies with the varying electrical current or voltage. The resonance frequency of the circuit can vary with the varying impedance of the circuit.

In these embodiments, the circuit can include an antenna. The analyte level of the user can be determined with the detected frequency characteristic and a frequency calibration value. The circuit can include at least one varactor diode. The second device can wirelessly detect the frequency characteristic of the circuit by inductively coupling with the circuit.

In these embodiments, the frequency characteristic can be a resonance frequency, and the circuit can be a first variable impedance circuit, and where detecting the resonance frequency of the circuit can include: applying a voltage to a second variable impedance circuit of the second device; propagating, by the second device, a plurality of sweep frequencies to the first variable impedance circuit; capturing, by the second device, a response to the plurality of sweep frequencies; and determining, by the second device, the resonance frequency of the first variable impedance circuit. In these embodiments, determining, by the second device, the resonance frequency of the circuit, can include: detecting a dual peak frequency response; and determining a center frequency of the dual peak frequency response.

In these embodiments, determining the analyte level of the user based on the detected frequency characteristic can include applying a calibration value. The second device can be a reader device, and the method can further include using the reader device to read the calibration value from an NFC tag or optical bar code. The second device can be a reader device, and the method can further include downloading, by the reader device, the calibration value over a network. The first device can be an on body device, and the calibration value can be stored in memory of the on body device. The method can further include transmitting the calibration value from the on body device to the reader device.

In these embodiments, the frequency characteristic can be a resonance frequency, and the circuit can be a first variable impedance circuit, where detecting the resonance frequency of the circuit can include: setting a first receiving window of the second device; and propagating, by the second device, a first plurality of sweep frequencies to the first device. The bandwidth of the first receiving window can be smaller than and included within a bandwidth of the first plurality of sweep frequencies. The method can further include determining whether a resonance frequency of the circuit is detected within the receiving window. The method can further include, if the resonance frequency of the circuit is not detected within the first receiving window, setting a second receiving window of the second device and propagating, by the second device, a second plurality of sweep frequencies to the first device. The first and second receiving windows can be different. The first and second receiving windows can be such that they do not overlap. The first and second pluralities of sweep frequencies can be the same or different. The first plurality of sweep frequencies can be commensurate with the first receiving window. The second plurality of sweep frequencies can be commensurate with the second receiving window.

In these embodiments, the method can further include outputting the analyte level of the user on a display. The method can further include outputting the analyte level of the user on a display of the second device.

In these embodiments, the analyte sensor can be a self-biased analyte sensor. The analyte sensor can output the electrical current or voltage that corresponds to the analyte level of the user without power from an artificial power source. The analyte level can be a glucose level.

In many embodiments, a system for detecting an analyte sensor measurement is provided, the system including: a first device including: an analyte sensor adapted to output an electrical current or voltage that corresponds to an analyte level of a user; and a circuit coupled with the analyte sensor, where the circuit has a frequency characteristic adapted to vary according to the electrical current or voltage output by the analyte sensor; and a second device adapted to wirelessly detect the frequency characteristic of the circuit and determine the analyte level of the user based on the detected frequency characteristic.

In these embodiments, the frequency characteristic can be a resonance frequency. The circuit can have an impedance that varies according to the electrical current or voltage. The circuit can include a component having a capacitance that varies according to the electrical current or voltage. The circuit can include an antenna. The circuit can include at least one varactor diode. The second device can be adapted to wirelessly detect the frequency characteristic of the circuit by inductive coupling with the circuit. The first device can be an on body device and the second device can be a reader device.

In these embodiments, the second device can include processing circuitry and a non-transitory memory on which instructions are stored that, when executed by the processing circuitry, cause the processing circuitry to determine the analyte level of the user with the detected frequency characteristic. The instructions, when executed by the processing circuitry, can cause the processing circuitry to determine the analyte level of the user with the detected frequency characteristic and a frequency calibration value. The first device can include non-transitory memory on which is stored the frequency calibration value. The frequency characteristic can be a resonance frequency, the circuit can be a first variable impedance circuit, and the second device can include a second variable impedance circuit. The instructions, when executed by the processing circuitry, can cause the processing circuitry to output a control voltage to the second variable impedance circuit. The second device can be configured such that the second variable impedance circuit sets a receiving window for the second device.

In these embodiments, the second device can further include a frequency generator adapted to output a plurality of sweep frequencies to the first device. The second device can include processing circuitry and a non-transitory memory on which instructions are stored that, when executed by the processing circuitry, can cause the processing circuitry to determine the plurality of sweep frequencies output by the frequency generator.

In these embodiments, the second device further can include a receiver adapted to induce or capture a response from the first device. The second device can include processing circuitry and a non-transitory memory on which instructions are stored that, when executed by the processing circuitry, can cause the processing circuitry to determine the frequency characteristic of the circuit from the captured response.

In these embodiments, the second device can include processing circuitry and a non-transitory memory on which instructions are stored that, when executed by the processing circuitry, cause the processing circuitry to determine the frequency characteristic of the circuit by detection of a dual peak frequency response. The instructions, when executed by the processing circuitry, can cause the processing circuitry to determine a center frequency of the dual peak frequency response. The instructions, when executed by the processing circuitry, can cause the processing circuitry to determine the analyte level of the user from at least the center frequency of the dual peak frequency response.

In these embodiments, the second device can include a user interface into which a frequency calibration value for the circuit can be input. The second device can be adapted to wirelessly receive a frequency calibration value for the circuit from the first device. The second device can be adapted to download a frequency calibration value for the circuit over a network.

In these embodiments, the second device can include processing circuitry and a non-transitory memory on which instructions are stored that, when executed by the processing circuitry, cause the processing circuitry to set a first receiving window of the second device and cause propagation of a first plurality of sweep frequencies to the first device. The bandwidth of the first receiving window can be smaller than and included within a bandwidth of the first plurality of sweep frequencies. The instructions, when executed by the processing circuitry, can cause the processing circuitry to determine whether a resonance frequency of the circuit is detected within the receiving window. The instructions, when executed by the processing circuitry, can cause the processing circuitry to, if the resonance frequency of the circuit is not detected within the first receiving window, set a second receiving window of the second device and cause propagation of a second plurality of sweep frequencies to the first device. The first and second receiving windows can be different. The first and second receiving windows can be such that they do not overlap. The first and second pluralities of sweep frequencies can be the same. The first and second pluralities of sweep frequencies can be different. The first plurality of sweep frequencies can be commensurate with the first receiving window. The second plurality of sweep frequencies can be commensurate with the second receiving window.

In these embodiments, the second device can further include a display adapted to output the analyte level of the user. The analyte sensor can be a self-biased analyte sensor. The analyte sensor can be adapted to output the electrical current or voltage that corresponds to the analyte level of the user without power from an artificial power source. The analyte level can be a glucose level.

In many embodiments, a device for detecting an analyte sensor measurement is provided, the device including: an analyte sensor adapted to output an electrical current or voltage that corresponds to an analyte level of a user; and a circuit coupled with the analyte sensor, where the circuit has a frequency characteristic adapted to vary according to the electrical current or voltage output by the analyte sensor.

In these embodiments, the device can be configured as an on body device. The circuit can have an impedance that varies according to the electrical current or voltage. The circuit can include a component having a capacitance that varies according to the electrical current or voltage. The circuit can include an antenna. The device can include a non-transitory memory on which is stored a frequency calibration value. The analyte sensor can be a self-biased analyte sensor. The analyte sensor can be adapted to output the electrical current or voltage that corresponds to the analyte level of the user without power from an artificial power source. The circuit can include at least one varactor diode. The circuit can include an inductor and a capacitor.

In many embodiments, a reader device for detecting an analyte sensor measurement is provided, the reader device including: processing circuitry; and non-transitory memory on which is stored a plurality of instructions that, when executed, cause the processing circuitry to cause propagation of a plurality of sweep frequencies to a sensor device, detect a frequency characteristic of the sensor device, and determine an analyte level of a user of the sensor device based on the detected frequency characteristic.

In these embodiments, the frequency characteristic can be a resonance frequency. The instructions, when executed by the processing circuitry, can cause the processing circuitry to determine the analyte level of the user with the detected frequency characteristic and a frequency calibration value.

In these embodiments, the reader device can further include a variable impedance circuit. The instructions, when executed by the processing circuitry, can cause the processing circuitry to output a control voltage to the variable impedance circuit. The reader device can be configured such that a voltage applied to the variable impedance circuit sets a receiving window for the reader device.

In these embodiments, the reader device can include a frequency generator adapted to output a plurality of sweep frequencies. The instructions, when executed by the processing circuitry, can cause the processing circuitry to control the plurality of sweep frequencies output by the frequency generator.

In these embodiments, the reader device can further include a receiver adapted to induce and/or capture a response from the sensor device. The instructions, when executed by the processing circuitry, can cause the processing circuitry to determine the frequency characteristic of the sensor device from the captured response.

In these embodiments, the instructions, when executed by the processing circuitry, can cause the processing circuitry to determine the frequency characteristic of the circuit by detection of a dual peak frequency response. The instructions, when executed by the processing circuitry, can cause the processing circuitry to determine a center frequency of the dual peak frequency response. The instructions, when executed by the processing circuitry, can cause the processing circuitry to determine the analyte level of the user from at least the center frequency of the dual peak frequency response.

In these embodiments, the reader device can further include a user interface into which a frequency calibration value for the sensor device can be input, where the instructions, when executed by the processing circuitry, cause the processing circuitry to use the frequency calibration value to determine the analyte level of the user. The reader device can be adapted to wirelessly receive a frequency calibration value for the sensor device. The reader device can be adapted to download a frequency calibration value for the sensor device over a network.

In these embodiments, the instructions, when executed by the processing circuitry, can cause the processing circuitry to set a first receiving window of the device and cause propagation of a first plurality of sweep frequencies to the sensor device. The bandwidth of the first receiving window can be smaller than and included within a bandwidth of the first plurality of sweep frequencies. The instructions, when executed by the processing circuitry, can cause the processing circuitry to determine whether a resonance frequency of the sensor device is detected within the receiving window. The instructions, when executed by the processing circuitry, can cause the processing circuitry to, if the resonance frequency of the sensor device is not detected within the first receiving window, set a second receiving window and cause propagation of a second plurality of sweep frequencies to the sensor device. The first and second receiving windows can be different. The first and second receiving windows can be such that they do not overlap. The first and second pluralities of sweep frequencies can be the same or different. The first plurality of sweep frequencies can be commensurate with the first receiving window. The second plurality of sweep frequencies can be commensurate with the second receiving window.

In these embodiments, the analyte level can be a glucose level. The reader device can be adapted to wirelessly detect the frequency characteristic of the circuit by inductive coupling with the circuit.

Computer program instructions for carrying out operations in accordance with the described subject matter may be written in any combination of one or more programming languages, including an object oriented programming language such as Java, JavaScript, Smalltalk, C++, C#, Transact-SQL, XML, PHP or the like and conventional procedural programming languages, such as the "C" programming language or similar programming languages. The program instructions may execute entirely on the user's computing device (e.g., reader) or partly on the user's computing device. The program instructions may reside partly on the user's computing device and partly on a remote computing device or entirely on the remote computing device or server, e.g., for instances where the identified frequency is uploaded to the remote location for processing. In the latter scenario, the remote computing device may be connected to the user's computing device through any type of network, or the connection may be made to an external computer.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A system for detecting an analyte sensor measurement, the system comprising:
   a first device comprising:
      an analyte sensor configured to output an electrical current or a voltage that corresponds to an analyte level of a user; and
      a circuit coupled with the analyte sensor, wherein the circuit has a frequency characteristic configured to vary according to the electrical current or the voltage output by the analyte sensor; and
   a second device configured to wirelessly detect the frequency characteristic of the circuit and determine the analyte level of the user based on the detected frequency characteristic;
   wherein the second device comprises processing circuitry and a non-transitory memory on which instructions are stored that, when executed by the processing circuitry, cause the processing circuitry to set a first receiving window of the second device and cause propagation of a first plurality of sweep frequencies to the first device.

2. The system of claim 1, wherein the frequency characteristic is a resonance frequency.

3. The system of claim 1, wherein the second device further comprises a frequency generator configured to output the first plurality of sweep frequencies to the first device.

4. The system of claim 1, wherein the second device further comprises a receiver configured to induce or capture a response from the first device, and wherein the instructions, when executed by the processing circuitry, cause the processing circuitry to determine the frequency characteristic of the circuit from the captured response.

5. The system of claim 1, wherein the instructions, when executed by the processing circuitry, cause the processing circuitry to:
   determine the frequency characteristic of the circuit by detection of a dual peak frequency response,
   determine a center frequency of the dual peak frequency response, and
   determine the analyte level of the user from at least the center frequency of the dual peak frequency response.

6. The system of claim 1, wherein the analyte sensor is a self-biased analyte sensor.

7. The system of claim 1, wherein the analyte sensor is configured to output the electrical current or the voltage that corresponds to the analyte level of the user without power from an artificial power source.

8. The system of claim 1, wherein the circuit comprises at least one varactor diode.

9. The system of claim 1, wherein the second device is configured to wirelessly detect the frequency characteristic of the circuit by inductive coupling with the circuit.

10. The system of claim 1, wherein the first device is an on body device and the second device is a reader device.

11. The system of claim 1, wherein the circuit has an impedance that varies according to the electrical current or the voltage.

12. The system of claim 11, wherein the circuit comprises a component having a capacitance that varies according to the electrical current or the voltage.

13. The system of claim 1, wherein the instructions, when executed by the processing circuitry, cause the processing circuitry to determine the analyte level of the user with the detected frequency characteristic.

14. The system of claim 13, wherein the instructions, when executed by the processing circuitry, cause the processing circuitry to determine the analyte level of the user with the detected frequency characteristic and a frequency calibration value.

15. The system of claim 13, wherein the frequency characteristic is a resonance frequency, wherein the circuit is a first variable impedance circuit, and wherein the second device comprises a second variable impedance circuit.

16. The system of claim 15, wherein the instructions, when executed by the processing circuitry, cause the processing circuitry to output a control voltage to the second variable impedance circuit, and wherein the second device is configured such that the second variable impedance circuit sets the first receiving window for the second device.

17. The system of claim 1, wherein a bandwidth of the first receiving window is smaller than and included within a bandwidth of the first plurality of sweep frequencies.

18. The system of claim 17, wherein the instructions, when executed by the processing circuitry, cause the processing circuitry to determine whether a resonance frequency of the circuit is detected within the first receiving window.

19. The system of claim 18, wherein the instructions, when executed by the processing circuitry, cause the processing circuitry to, if the resonance frequency of the circuit is not detected within the first receiving window, set a second receiving window of the second device and cause propagation of a second plurality of sweep frequencies to the first device.

* * * * *